(12) United States Patent
Looft et al.

(10) Patent No.: US 7,919,133 B2
(45) Date of Patent: Apr. 5, 2011

(54) SUBSTITUTED CYCLOPROPANECARBOXYLIC ACID (3-METHYL-CYCLOHEXYL)AMIDE AS FLAVORING SUBSTANCE

(75) Inventors: Jan Looft, Holzminden (DE); Tobias Vössing, Beverungen (DE); Jakob Ley, Holzminden (DE); Michael Backes, Holzminden (DE); Maria Blings, Holzminden (DE)

(73) Assignee: SYMRISE GmbH & Co. KG, Holzminden (DE)

(*) Notice: Subject to any disclaimer, the term of this patent is extended or adjusted under 35 U.S.C. 154(b) by 379 days.

(21) Appl. No.: 12/117,438

(22) Filed: May 8, 2008

(65) Prior Publication Data

US 2008/0292763 A1 Nov. 27, 2008

Related U.S. Application Data

(60) Provisional application No. 60/916,589, filed on May 8, 2007.

(51) Int. Cl.
*A23L 1/226* (2006.01)
*C07C 231/00* (2006.01)

(52) U.S. Cl. .......................... 426/538; 426/534; 564/190

(58) Field of Classification Search .................. None
See application file for complete search history.

(56) References Cited

U.S. PATENT DOCUMENTS

| | | | |
|---|---|---|---|
| 2,692,282 | A | 10/1954 | Brown |
| 3,159,585 | A | 12/1964 | Evans et al. |
| 3,277,171 | A | 10/1966 | Hopkins |
| 3,971,852 | A | 7/1976 | Brenner et al. |
| 4,518,615 | A | 5/1985 | Cherukuri et al. |
| 4,532,145 | A | 7/1985 | Saleeb et al. |
| 5,093,136 | A | 3/1992 | Panhorst et al. |
| 5,124,162 | A | 6/1992 | Boskovic et al. |
| 5,266,336 | A | 11/1993 | McGrew et al. |
| 5,601,858 | A | 2/1997 | Mansukhani et al. |
| 2004/0202619 | A1 | 10/2004 | Dewis et al. |
| 2004/0202760 | A1 | 10/2004 | Dewis et al. |
| 2005/0084506 | A1 | 4/2005 | Tachdjian et al. |

FOREIGN PATENT DOCUMENTS

| | | |
|---|---|---|
| EP | 0242325 | 10/1987 |
| EP | 1258200 | 11/2002 |
| WO | WO-04000787 | 12/2003 |
| WO | WO-2004043906 | 5/2004 |
| WO | WO-2004056745 | 7/2004 |
| WO | WO-2004078302 | 9/2004 |
| WO | WO-2005020897 | 3/2005 |
| WO | WO-2005096841 | 10/2005 |
| WO | WO-2006024587 | 3/2006 |
| WO | WO-2006058893 | 6/2006 |
| WO | WO-2006099762 | 9/2006 |
| WO | WO-2006106023 | 10/2006 |
| WO | WO-2007003527 | 1/2007 |
| WO | WO-2007014879 | 2/2007 |
| WO | WO-2007107596 | 9/2007 |

OTHER PUBLICATIONS

K. Mylavarapu, et al., "Boric Acid Catalyzed Amidation in the Synthesis of Action Phramaceutical Ingredients," Organic Process Research & Development, vol. 11, No. 6, 2007, pp. 1065-1068.
O. Wallach, "Zur Kenntniss der Terpene and der ätherischen Oele," Ann. Chem. 1893, 276, 296-313.
T. Shimizu, et al., "Chloromethanesulfonate as an Efficient Leaving Group: Rearrangement of the Carbon-Carbon Bond and Conversion of Alcohols into Azides and Nitriles," Synthesis, 1999, No. 8, pp. 1373-1385.
A. Bose, et al., "A Convenient Synthesis of Axial Amines," J. Am. Chem. Soc. 1962, vol. 27, pp. 2925-2927.

*Primary Examiner* — Keith D Hendricks
*Assistant Examiner* — Nikki H Dees
(74) *Attorney, Agent, or Firm* — Connolly Bove Lodge & Hutz LLP

(57) ABSTRACT

The present invention relates to the use of a compound of formula (I) or a mixture of compounds of formula (I)

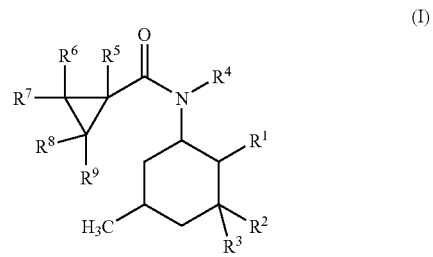

(I)

wherein:
$R^1$, $R^2$, and $R^3$ are independently H or an alkyl group having 1 to 3 C-atom, wherein at least one of $R^1$, $R^2$, and $R^3$ is not H;
$R^4$ is H, an alkyl group having 1 to 6 C-atom, or an alkenyl group having 2 to 6 C-atom;
$R^5$, $R^6$, $R^7$, and $R^8$ are independently H or methyl; and
$R^9$ is H, an alkyl group having 5 to 12 C-atoms, or an alkenyl group having 5 to 12 C-atoms;
as a flavoring substance or mixture of flavoring substances.

19 Claims, 1 Drawing Sheet

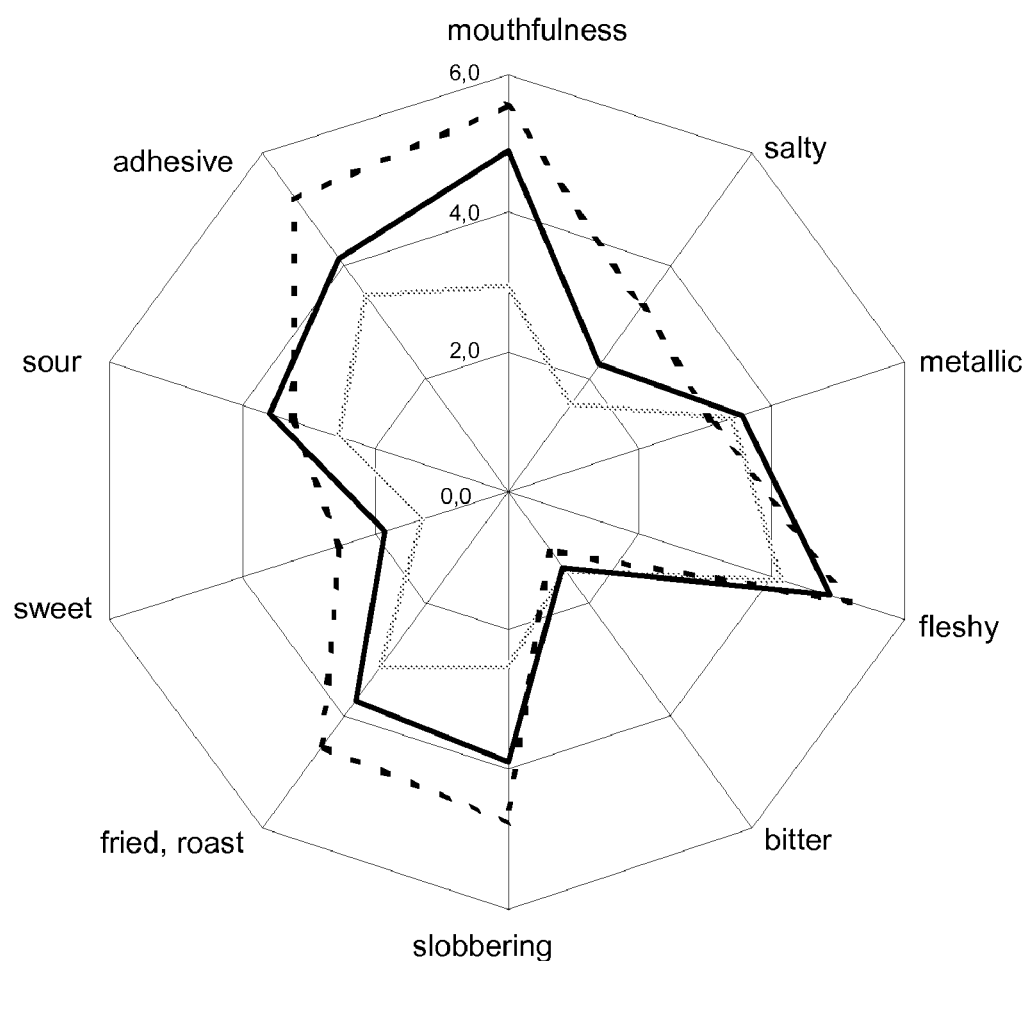

SUBSTITUTED CYCLOPROPANECARBOXYLIC ACID (3-METHYL-CYCLOHEXYL)AMIDE AS FLAVORING SUBSTANCE

This application claims the benefit of U.S. Provisional Patent Application No. 60/916,589 filed on May 8, 2007, the disclosures of which is hereby incorporated by reference herein in its entirety.

The present invention relates to the use of substituted cyclopropanecarboxylic acid (3-methyl-cyclohexyl)amides of formula (I) (see below) as flavoring substances. The compounds are especially suitable for creating, modifying or enhancing an Umami-taste. The present invention further relates to compositions and semi-finished goods, which comprise a flavorfully effective amount of said compounds as well as a method for creating, modifying and/or enhancing taste impressions, in particular, Umami. Finally the present invention also relates to novel compounds, which provide special taste impressions.

Flavoring substances and compounds with unusual sensory properties, which carry an amide group, have been known for long time. So many important coolants such as WS3, WS5 und WS23 have an amide structure:

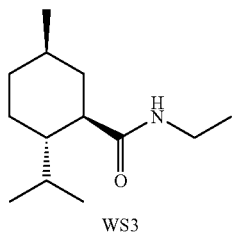
WS3

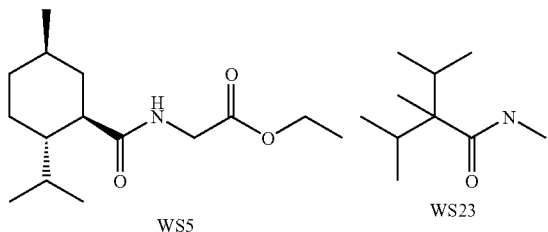
WS5    WS23

The hot substances capsaicin from chilli pod and the piperine of white pepper are likewise among the sensorially significant amides. The inartificial alkamides pellitorine and spilanthole show a prolonged and numbing effect in the mouth besides a salivary-stimulating and prickling effect:

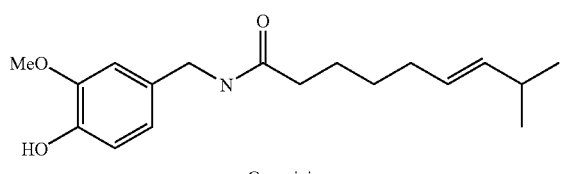
Capsaicin

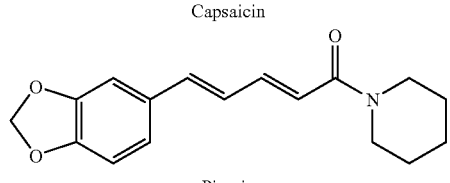
Piperin

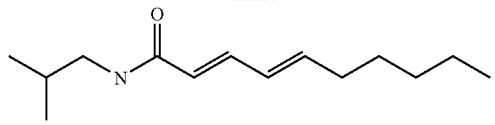
Pellitorin

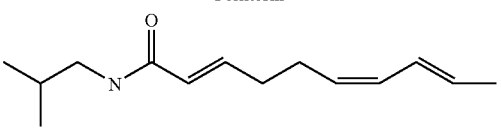
Spilanthol

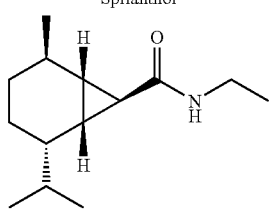
SY 5757

Regarding the chemical structure of spilanthols, various alkylidene amides are provided in the publication US 2004/0202760 and US 2004/0202619, which cover quite different sensory impressions such as prickling, numbness, bitterness, mouthfulness, richness, etc. For some compounds such as N-cyclopropyl-E2,Z6-nonadiene amide, N-ethyl-E2,Z6-dodecadiene amide and N-ethyl-E2,Z6-nonadiene amide, an effect similar to MSG (MSG =monosodium glutamate, sodium glutamate) or an impression similar to Umami is given.

Publication US 2005/084506 describes a huge number of supposedly more taste-active non-natural amides.

In US-Patent application 60/829,958 filed on Oct. 18, 2006—regarding a menthol skeletal structure, a new artificial flavoring substance which is especially suitable for creating, modifying and enhancing an Umami taste, is described.

Several documents address themselves to substituted cyclopropanecarboxylic acid(3-methyl-cyclohexyl)amides in the broadest sense and describe their pharmacological effects.

WO 2004/056745 describes amines of formula

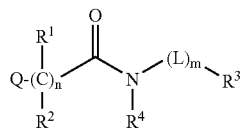

as 11-Beta hydroxylsteroid dehydrogenase inhibitors. However, the general formula in this document is so broadly interpreted that a large number of compounds can be covered thereby, that only concrete information, such as that disclosed from claim 3 in said document can be taken as the disclosure of individual compound or a group of compounds with common properties. So the compounds known for long time such as above-mentioned WS3 also fall within the above general formula (m, m=0, $R^3$=$C_1$-$C_8$ alkyl, $R^1$, $R^2$, $R^4$ are hydrogen and Q is $C_3$-$C_8$ cycloalkyl with up to three alkyl substituents). The taste of compounds of WO 2004/056745 is not described.

WO 2005/020897 describes various derivates of menthols as Trp-p8 antagonists.

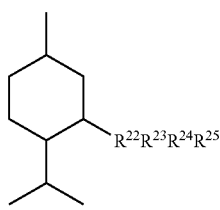

However, the general formula here is also very broadly interpreted ($R^{22}$ inter alia amide group, $R^{23}$ inter alia aliphatic group having up to 25 C atoms as well as $R^{24}$ and $R^{25}$=H), so that WS3 is again covered thereby. The following compound is also possible according to WO 2005/020897 (Ref. No.: 2013):

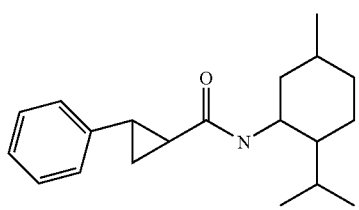

The taste of the claimed compounds is not discussed in this document either.

EP 1632 483 addresses itself to heterocyclic substituted carbonyl derivates as ligands for the dopamine D3 receptor. Nothing about the taste is disclosed in this document either.

In addition, a structure which is commercially available by CAPLUS Search [CAS 492426-03-6] is well known.

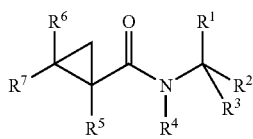

There is no statement about the taste of this compound either.

Furthermore, three documents which report the taste or the cooling effect of cyclopropyl carboxylic acid derivatives or substituted cyclohexyl amides are known.

EP 1642 886 describes inter alia cyclopropyl carboxylic acid derivates with the following structure,

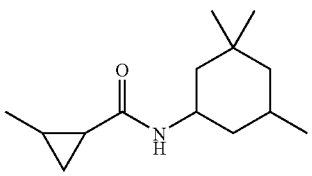

which are used for creating, modifying and/or enhancing at least one of the five basic taste types. However, the focus here is unsaturated amines. All structures are based on di-alkylated amides, and if cyclohexyl residues are possible, these are necessarily unsubstituted.

WO 2006/099762 describes the use of various substituted benzoic amides as coolants. The compound based on menthol amine has the strongest ascertained cooling effect.

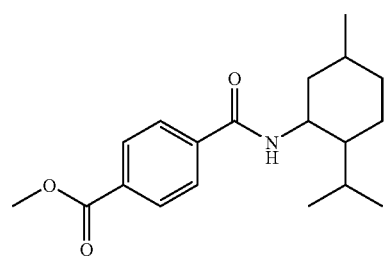

Document DE 2516610 of 1975 discloses the use of various carboxylic acid derivates (inter alia also amides) as cooling substances. However, the general formula is very unspecific and in the examples, which disclose cyclopropanecarboxylic acid, no substituted cyclohexyl amines are used.

There is further a need to find new flavoring substances and flavorings, taste-active compounds or compounds, which can create, modify or enhance the flavor. In particular, there is a need for the compounds, which can induce or enhance the taste impression of "Umami".

Hence, the object of the present invention is to provide a means which can create, modify or enhance the desired taste notes.

This object is achieved according to the invention by the use of a compound of formula (I)

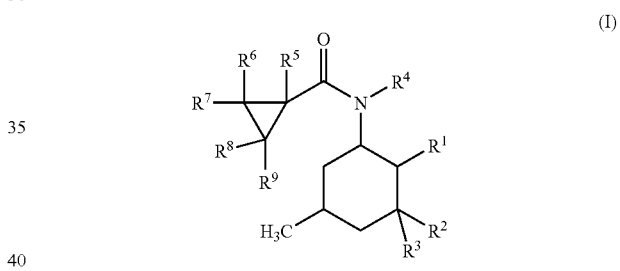

(I)

wherein:
$R^1$, $R^2$, $R^3$ in each case independently of each other represents hydrogen or an alkyl group having 1 to 3 C-atoms, in particular methyl, ethyl, n-propyl or iso-propyl, wherein at least one group is not H;
$R^4$ represents hydrogen, an alkyl group having 1 to 6 C-atoms, in particular methyl, ethyl, n-propyl, iso-propyl, n-butyl, iso-butyl, sec-butyl, tert-butyl, n-pentyl, 1-methyl-butyl, 2-methyl-butyl, 3-methyl-butyl, 1,2-dimethyl-propyl, 1,1-dimethyl-propyl, 2,2-dimethyl-propyl, n-hexyl, 1-methyl-pentyl, 2-methyl-pentyl, 3-methyl-pentyl, 4-methyl-pentyl, 1-ethyl-butyl, 2-ethyl-butyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-1-methyl-propyl, 1-ethyl-2-methyl-propyl, 1,1,2-trimethyl-propyl or 1,2,2-trimethyl-propyl, or an alkenyl group having 2 to 6 C-atoms, in particular 1-propenyl, 2-propenyl, 1-methyl-1-propenyl, 2-methyl-1-propenyl or 2-methyl-2-propenyl;
$R^5$, $R^6$, $R^7$, $R^8$ in each case independently of each other represents hydrogen or methyl;
$R^9$ represents hydrogen, an alkyl group having 4 to 12 C-atoms, in particular n-butyl, iso-butyl, sec-butyl, tert-butyl, n-pentyl, 1-methyl-butyl, 2-methyl-butyl, 3-methyl-butyl, 1,2-dimethyl-propyl, 1,1-dimethyl-propyl, 2,2-dimethyl-propyl, n-hexyl, 1-methyl-pentyl, 2-methyl-pentyl, 3-methylpentyl, 4-methyl-pentyl, 1-ethyl-butyl, 2-ethyl-butyl, 1,1-dimethyl-butyl, 1,2-dimethyl-butyl, 1,3-dimethyl-butyl, 2,2-dimethyl-butyl, 2,3-dimethylbutyl, 3,3-dimethyl-butyl, 1-ethyl-1-methyl-propyl, 1-ethyl-2-methylpropyl, 1,1,2-trimethyl-propyl, 1,2,2-trimethyl-propyl, n-heptyl, n-octyl, n-nonyl, n-decyl, n-undecyl or n-dodecyl or an alkenyl group having 4 to 12 C-atoms, in particular 1-methyl-1-propenyl, 2-methyl-1-propenyl or 2-methyl-2-propenyl as a flavoring substance or a mixture of flavoring substances.

Preferably, the compounds of formula (I) according to the present invention, in which a compound or the compounds of formula (I) is a compound or are compounds selected from the group consisting of:

(1) (1R,3S)-2,2-dimethyl-3-(2-methyl-propenyl) -cyclopropanecarboxylic acid-((1S,2S,5R)-2-isopropyl-5-methyl-cyclohexyl)-amide
(2) (1R,3S)-2,2-dimethyl-3-(2-methyl-propenyl) -cyclopropanecarboxylic acid-((1R,2R,5S)-2-isopropyl-5-methyl-cyclohexyl)-amide
(3) (1S,3R)-2,2-dimethyl-3-(2-methyl-propenyl) -cyclopropanecarboxylic acid-((1S,2S,5R)-2-isopropyl-5-methyl-cyclohexyl)-amide
(4) (1S,3R)-2,2-dimethyl-3-(2-methyl-propenyl) -cyclopropanecarboxylic acid-((1R,2R,5S)-2-isopropyl-5-methyl-cyclohexyl)-amide
(5) (1S,3S)-2,2-dimethyl-3-(2-methyl-propenyl) -cyclopropanecarboxylic acid-((1S,2S,5R)-2-isopropyl-5-methyl-cyclohexyl)-amide
(6) (1S,3S)-2,2-dimethyl-3-(2-methyl-propenyl) -cyclopropanecarboxylic acid-((1R,2R,5S)-2-isopropyl-5-methyl-cyclohexyl)-amide
(7) (1R,3R)-2,2-dimethyl-3-(2-methyl-propenyl) -cyclopropanecarboxylic acid-((1S,2S,5R)-2-isopropyl-5-methyl-cyclohexyl)-amide
(8) (1R,3R)-2,2-dimethyl-3-(2-methyl-propenyl) -cyclopropanecarboxylic acid-((1R,2R,5S)-2-isopropyl-5-methyl-cyclohexyl)-amide

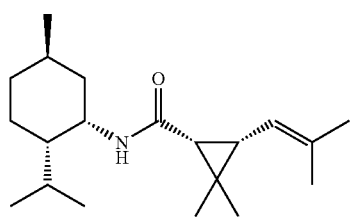
(1)

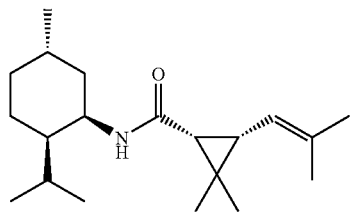
(2)

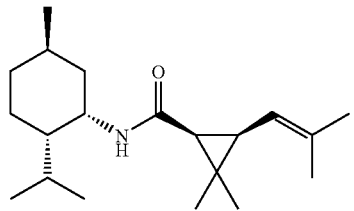
(3)

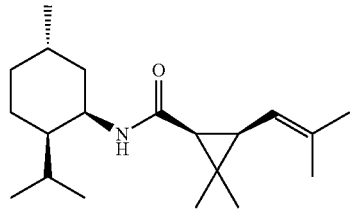
(4)

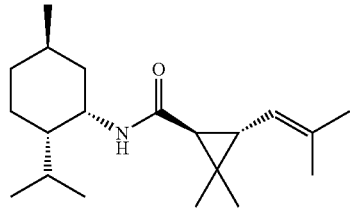
(5)

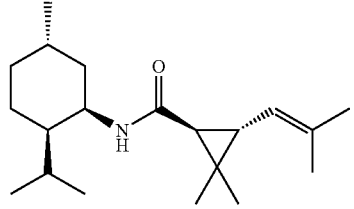
(6)

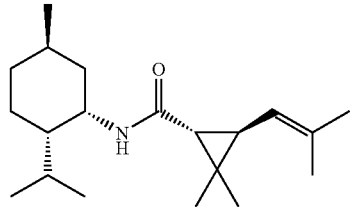
(7)

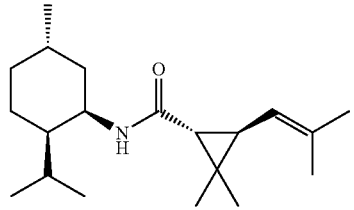
(8)

With the search for such compounds, it was surprisingly found that—unlike the above -mentioned prior art suggested—certain substituted cyclopropanecarboxylic acid (3-methylcyclohexyl)amides of formula (I) are not coolants, but have a distinctive Umami character.

The meaning of a defined substitution manner on cyclohexane skeleton is further underpinned by the fact that the unsubstituted cyclohexane derivate

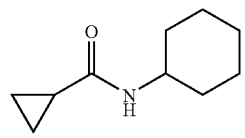

not according to the present invention—on the basis of EP 1642886 shown—is rated as taste-neutral with tasting in our own investigations. In particular, no creating or enhancing of an Umami taste impression could be verified even in American beef extract.

In a embodiment of the use according to the present invention, it is further preferred, if the compound or the compounds of formula (I), in which groups $R^2$, $R^3$, $R^4$, $R^5 R^6$, $R^7$, $R^8$ in each case represents hydrogen, and thus is or are a compound of formula (II)

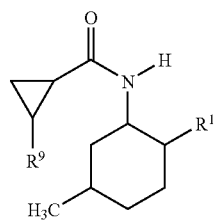

(II)

(II) wherein:

$R^1$ represents an alkyl group having 1 to 3 C-atoms, in particular methyl, ethyl, n-propyl or i-propyl.

$R^9$ represents hydrogen, an alkyl group having 4 to 12 C-atoms, in particular n-butyl, iso-butyl, sec-butyl, tert-butyl, n-pentyl, 1-methyl-butyl, 2-methyl-butyl, 3-methyl-butyl, 1,2-dimethyl-propyl, 1,1-dimethyl-propyl, 2,2-dimethyl-propyl, n-hexyl, 1-methyl-pentyl, 2-methyl-pentyl, 3-methylpentyl, 4-methyl-pentyl, 1-ethyl-butyl, 2-ethyl-butyl, 1,1-dimethyl-butyl, 1,2-dimethyl-butyl, 1,3-dimethyl-butyl, 2,2-dimethyl-butyl, 2,3-dimethylbutyl, 3,3-dimethyl-butyl, 1-ethyl-1-methyl-propyl, 1-ethyl-2-methylpropyl, 1,1,2-trimethyl-propyl, 1,2,2-trimethyl-propyl, n-heptyl, n-octyl, n-nonyl, n-decyl, n-undecyl or n-dodecyl or an alkenyl group having 4 to 12 C-atoms, in particular methyl-1-propenyl, 2-methyl-1-propenyl or 2-methyl-2-propenyl.

Particularly preferably, the compounds of formula (II) according to the present invention are mixtures or single substances of following compounds:

(9) Cyclopropanecarboxylic acid-((1R,2S,5R)-2-isopropyl-5-methyl-cyclohexyl)amide
(10) Cyclopropanecarboxylic acid-((1S,2R,5S)-2-isopropyl-5-methyl-cyclohexyl)amide
(11) Cyclopropanecarboxylic acid-((1S,2S,5R)-2-isopropyl-5-methyl-cyclohexyl)amide
(12) Cyclopropanecarboxylic acid-((1R,2R,5S)-2-isopropyl-5-methyl-cyclohexyl)amide
(13) Cyclopropanecarboxylic acid-((1R,2R,5R)-2-isopropyl-5-methyl-cyclohexyl)amide
(14) Cyclopropanecarboxylic acid-((1S,2S,5S)-2-isopropyl-5-methyl-cyclohexyl)amide
(15) Cyclopropanecarboxylic acid-((1S,2R,5R)-2-isopropyl-5-methyl-cyclohexyl)amide
(16) Cyclopropanecarboxylic acid-((1R,2S,5S)-2-isopropyl-5-methyl-cyclohexyl)amide

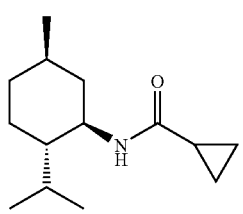

(9)

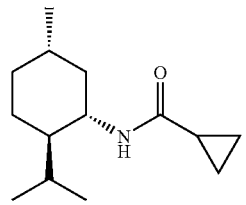

(10)

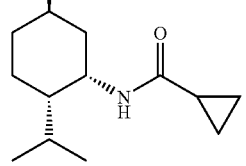

(11)

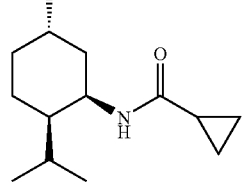

(12)

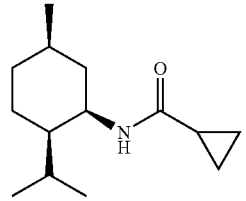

(13)

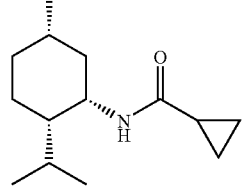

(14)

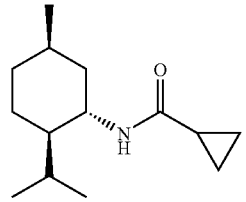

(15)

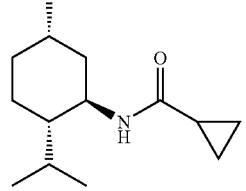

(16)

Because of their interesting and strong Umami-properties, the compounds of formulas (11) and (12) or a mixture comprising or consisting of the compounds of formulas (11) and (12) are particularly preferred.

A mixture, which consists of or comprises the following components is further particularly preferred:

(a) a compound selected from the compounds of formulas (11) and (12) or a mixture consisting of the compounds of formulas (11) and (12)
and
(b) a compound selected from the group consisting of the compounds of formulas (9), (10), (13), (14), (15) and (16) or a mixture consisting of two or more compounds selected from the group consisting of the compounds of formulas (9), (10), (13), (14), (15) and (16).

In the mixture defined above, the weight ratio of (a) the compounds of formulas (11) and (12) as a whole to (b) the compounds of formulas (9), (10), (13), (14), (15) and (16) as a whole is preferably at least 60:40, further preferably at least 90:10, in particular preferably 95:5.

A further aspect of the present invention relates to compositions, in particular compositions suitable for consumption, comprising or consisting of
(i) a flavorfully effective amount of one or more compounds of formulas (11) and (12) or a mixture as defined above, consisting of (a) one or more compounds of formulas (11) and (12) as well as (b) one or more compounds of formulas (9), (10), (13), (14), (15), (16); and
(ii) one or more other ingredients suitable for consumption.

Regarding preferred compounds and mixtures, the above-mentioned preferred compounds and mixtures applies here accordingly.

In spider diagram attached as FIG. 1, American beef broth is exemplarily compared as a base, with firstly such a base with an addition of 5 ppm of mixture of cyclopropanecarboxylic acid-((1S,2S,5R)-2-isopropyl-5-methyl-cyclohexyl)-amide (11) and Cyclopropanecarboxylic acid-((1R,2R,5S)-2-isopropyl-5-methyl-cyclohexyl)-amide (12) (mixing ratio of 1:1) and secondly with such a base with an addition of 0.05 wt.-% of MSG. It is clear that the above-mentioned compounds possess a distinct Umami taste, which is very similar to the sodium glutamate in the profile.

Our own studies have shown that compounds of formula (I) or (II) to be used according to the present invention can create, modify and/or enhance very well an Umami-taste, both in initial taste (Impact) and in the longer-persistent taste perception, in highly sodium glutamate-reduced or sodium glutamate-free foods, for example in spicy foods such as tomato soup, chicken soup, cookies, ready-to-use pizza, potato chips and popcorn. And therefore the taste experience is found pleasant in many cases even preferable to sodium glutamate.

Accordingly, a part of the invention is also the use of a compound or a mixture of compounds of formula (I) or (II) as defined above according to the present invention for creating, modifying or enhancing an Umami-taste.

Another aspect of the present invention relates to compositions, in particular the compositions suitable for consumption, comprising or consisting of an flavorfully effective amount of one or more compounds of formula (I) or (II) as well as one or more other ingredients suitable for consumption. Regarding the compounds of formula (I) or (II) to be used in the composition according to the present invention, those described above apply here accordingly.

The preparations (compositions) used for nourishment, oral care or enjoyment according to the present invention are regular products that are intended to be introduced into the human oral cavity, to remain therein for a certain time and then either be consumed (e.g. ready-to-consume food, see also below) or be removed from the mouth (e.g. chewing gum and toothpaste). These products include all materials or substances that are intended to be taken up by human in a processed, partially processed or unprocessed state. This also includes the materials, which are added to the foods in their preparation, processing or handling, and are intended to be introduced into the human oral cavity.

In the context of the present text, the term "food" is understood in particular as the materials that are intended to be swallowed by human in an unchanged, prepared or processed state, and then digested. Food is also understood as coverings, coatings or other enclosures, which are intended to be swallowed together, or are predicted to be swallowed. Certain products, which are usually removed again from the oral cavity (e.g. chewing gum), are also understood as food in the context of the present text, because it can not be excluded that they are at least partly swallowed.

The ready-to-consume food is herein understood as the food, which is already fully composed as to the substances which are decisive for the taste. The term "ready-to-consume food" also covers beverages and solid or semi-solid ready-to-consume food. The so-called deep-frozen products, which must be thawed and warmed up to consumption temperature before consumption, can be mentioned as examples. The products such as yoghurt or ice cream or chewing gum also belong to the ready-to-consume foods.

The oral care products (also called oral hygiene product or oral hygienic preparation) for the purposes of the present invention are understood as a formulation familiar to the person skilled in the art, which is used for cleaning and caring the oral cavity and pharyngeal space, and for refreshing the breath. The care of the teeth and gums is here explicitly included. Dosage forms of usual oral hygienic formulations are, in particular, creams, gels, pastes, foams, emulsions, suspensions, aerosols, sprays, as well as capsules, granules, pastilles, tablets, candy or chewing gum, but this listing should not be understood as a limitation to the present invention.

Preferred oral care products (oral hygiene product) are particularly those in the form of toothpaste, tooth cream, tooth gel, tooth powder, tooth cleaning liquid, tooth cleaning foam, mouthwash, toothpaste and mouthwash as a 2-in-1 product, lolly, mouth spray, dental floss, chewing gum for dental care.

Chewing gum generally comprises a chewing gum base, i.e. a chewing mass which becomes plastic while chewing, various types of sugar, sugar substitutes, other sweetly tasting substances, sugar alcohols (especially sorbitol, xylitol, mannitol), cooling active substances, taste modifier for unpleasant taste impressions, other taste-modifying substances (for example inositol phosphate, nucleotide such as guanosine monophosphate, adenosine monophosphate or other substances such as sodium glutamate or 2-phenoxypropionic acid), humectants, thickeners, emulsifiers, stabilizers, odor modifier and flavorings (for example eucalyptus menthol, cherry, strawberry, grapefruit, vanilla, banana, citrus, peach, black currant, tropical fruits, ginger, coffee, cinnamon, combinations of (the mentioned flavorings) with mint flavourings as well as spearmint and peppermint alone). The combination of flavorings with other substances, which have cooling, warming and/or slobbering properties, is also especially interesting.

Numerous different chewing gum bases are known from prior art, in which a distinction has been made between so-called "chewing gum" and "bubble gum" bases, wherein the latter is softer so that with which chewing gum bubbles can also be formed. Common chewing gum bases currently comprise, besides traditionally used natural resins or natural latex chicle, mostly elastomers such as polyvinyl acetate (PVA), polyethylene, (low or medium molecular) polyisobutene (PIB), polybutadiene, isobutene-isoprene copolymers (butyl rubber), polyvinylethylether (PVE), polyvinylbutylether, copolymers of vinyl ester and vinyl ether, styrenel-butadiene-copolymers (styrene-butadiene-rubber, SBR) or vinylelastomers, for example those based on vinyl acetate/vinyl laurate, vinyl acetate/vinyl stearate or ethylene/vinyl acetate, and mixtures of so-called E-elastomers, for example, described in EP 0 242 325, U.S. Pat. Nos. 4,518,615, 5,093,136, 5,266,336 5,601,858 or 6,986,709. In addition, chewing gum bases comprise further ingredients such as (mineral) fillers, plasticizers, emulsifiers, antioxidants, waxes, fats or fatty oil, for example hardened (hydrogenated) vegetable or animal fat, mono-, di- or triglyceride. Suitable (mineral) fillers are for example calcium carbonate, titanium dioxide, silicon dioxide, talc, aluminium oxide, dicalcium phosphate, tricalcium phosphate, magnesium hydroxide and mixture thereof. Suitable plasticizers or agents for preventing adhesion are for example lanolin, stearic acid, sodium stearate, ethyl acetate, diacetine (gylcerol diacetate), triacetine (gylcerol triacetate), triethyl citrate. Suitable waxes are for example paraffin waxes, candelilla waxes, carnauba waxes, microcrystalline waxes and polyethylene waxes. Suitable emulsifiers are for example phosphatides such as lecithin, mono- and diglyceride of fatty acid, for example glycerol monostearate.

A series of compositions according to the present invention are preferred. A (preferably spray-dried) composition, which, in addition to one or more compounds of formula (I) or (II) to be used according to the present invention, comprises one or more solid carrier sub-stances suitable for consumption. Preferred compositions consist of the compound or the compounds of formula (I) or (II) to be used according to the present invention and the carrier substance or the carrier substances.

Carrier substances in these preferred (preferably spray-dried) compositions according to the present invention are advantageously silicon dioxide (silicic acid, silica gel), carbohydrates and/or carbohydrate polymers (polysaccharide), cyclodextrine, starches, degraded starches (starch hydrolysates), chemically or physically modified starches, modified celluloses, gum arabic, Ghatti-gum, traganth, karaya, carrageenan, guar gum, locust bean gum, alginate, pectin, Inulin or xanthan gum. Preferred starch hydrolysates are maltodextrines and dextrines.

Preferred carrier substances are silicon dioxide, gum arabic and maltodextrines, wherein maltodextrines with DE values in the range of 5 to 20 are preferred. It is irrelevant, which plant is originally used for preparing the starch hydrolysates from starch. Corn-based starches, and starches of tapioca, rice, wheat or potatoes are suitable and readily available. The carrier substances can also act as a flow adjuvant, for example silicon dioxide.

The compositions according to the present invention, which in addition to the compound or compounds of the Formula (I) or (II) to be used according to the invention, comprises one or more solid carrier substances, for example, can be prepared by mechanical mixing process, in which a comminuting of the existing particle can also be carried out at the same time, or by spray drying. The compositions according to the present invention, which comprise solid carrier substances and are prepared by spray drying, are preferred. Regarding spray drying, references are made to U.S. Pat. Nos. 3,159,585, 3,971,852, 4,532,145 or 5,124,162.

Preferred compositions according to the present invention, which comprise carrier sub-stances and are prepared by spray drying, have a mean particle size in the range of 30-300 µm and a residual moisture of less than or equal to 5 wt.-%.

The weight ratio of the total amount of the compounds of formula (I) or (II) to be used according to the present invention to the solid carrier substance or the carrier substances suitable for nourishment is preferably in the range of 1:10 to 1:100000, preferably in the range of 1:100 to 1:20000, especially preferably in the range of 1:1000 to 1:5000, based on the dry weight of the composition.

The sum of ingredients of (i) compounds of formula (I) or (II) to be used according to the present invention and (ii) the carrier substance or the carrier substances in the composition is preferably in the range of 70 to 100 wt.-%, preferably in the range of 85 to 100 wt.-%

The present invention also relates to a (preferably spray-dried) composition, which in addition to (i) one or more compounds of formula (I) or (II) to be used according to the present invention and (ii) solid carrier substances, comprises (iii) one or more flavoring components, or said composition consists of the above components.

Such a flavoring composition in the sense of the present invention comprises at least one volatile flavoring substance (this, however, does not mean compounds of formula (I) or (II)). The volatile flavoring substance is herein preferably a sensorially effective component with a vapor pressure of greater than or equal to 0.01 Pa at 25° C., preferably a vapor pressure of greater than or equal to 0.025 Pa at 25° C. A large part of the volatile flavoring substances have a vapor pressure of greater than or equal to 1 Pa at 25° C. These flavoring substances are considered as preferred for using in the compositions according to the present invention.

Examples of flavoring substances, which can be the ingredient of the flavoring composition, are found in, for example, K. Bauer, D. Garbe and H. Surburg, Common Fragrance and Flavor Materials, 4$^{th}$. Ed., Wiley-VCH, Weinheim 2001. The following are exemplarily listed: organic acids (saturated and unsaturated) such as butyric acid, acetic acid, methylbutyric acid, capronic acid; alcohols (saturated and unsaturated) such as ethanol, propylene glycol, octenol, cis-3-hexenol, benzyl alcohol; sulfides and disulfides such as dimethyl sulfide, difurfuryl disulfide, methylthiopropanal, thiols such as methylfuranthiol; pyrazines and pyrrolines such as methylpyrazine, acetylpyrazine, 2-propionylpyrroline, 2-acetyl pyrroline.

The flavoring composition can also be used in the form of reaction flavorings (Maillard products) and/or extracts or etheric oils from plants or plant parts or fractions thereof.

Another preferred composition suitable for consumption according to the present invention, which comprises one or more compounds of formula (I) or (II) to be used according to the invention, is a water-in-oil (W/O) emulsion. Besides the compound or the compounds of formula (I) or (II) to be used according to the invention, such an emulsion comprises water, an oil phase, one or more W/O emulsifiers, if necessary, one or more antioxidants and if necessary, one or more substances for enhancing an antioxidative effect.

Preferably, such a composition (W/O emulsion) according to the present invention comprises
  0.01 to 0.1 wt. % of one or more compounds of formula (I) or (II) used according to the present invention,
  5 to 30 wt.-%, preferably 8 to 25 wt. -% of water,
  50 to 90 wt.-%, preferably 60 to 80 wt.-% of an oil phase,
  0.1 to 5 wt.-% of consumable W/O emulsifier as well as;
  if necessary, one or more antioxidants and if necessary, one or more substances for enhancing an antioxidative effect.

It is particularly preferred that such a W/O emulsion according to the present invention consists of said ingredients in said amounts.

The oil phase of such a W/O emulsion according to the present invention preferably comprises (or consists of) a fatty oil and/or a flavoring component. Oil phases comprising or consisting of a fatty oil and a flavoring component are preferred.

Suitable fatty oils are, for example, edible oil, in particular vegetable oil. Suitable fatty oils are, for example, borage oil, thistle oil, peanut oil, hazelnut oil, coconut oil, pumpkin seed oil, linseed oil, corn oil, macadamia nut oil, almond oil, olive oil, palm kernel oil, pecan oil, pistachios oil, rapeseed oil, rice germ oil, sesame oil, soybean oil, sunflower oil, walnut oil or wheat germ oil, or fractions available from them. Liquid neutral ester based on medium chain fatty acids and glycerin, such as Miglyols (for example Miglyol 810, Miglyol 812), can also be used. Sunflower oil, palm kernel oil and rapeseed oil are preferred. Furthermore, fractionated coconut oil, which mainly contains fatty acid residues having 6 to 8 C-atoms, is preferably used. These distinguish themselves by their taste neutrality and their good oxidation stability.

The consumable W/O emulsifier is preferably selected from the group consisting of lecithin (E 322), mono- and diglycerides of edible fatty acids (E 471), acetic acid monoglycerides (E 472a), lactic acid monoglycerides (E 472b), citric acid monoglycerides (E 472c), tartaric acid monoglyceride (E 472d), diacetyl tartaric acid monoglycerides (E 472e), sorbitan monostearate (E 491).

Suitable antioxidants and substances, which can enhance the antioxidative effect, are natural tocopherols and their derivates, tocotrienols, flavonoids, ascorbic acid and salts thereof, alpha-hydroxy acids (for example citric acid, lactic acid, malic acid, tartaric acid) and Na-, K- and Ca-salts thereof, ingredients isolated from plants, extracts or fractions thereof, for example, from tea, green tea, algae, grape corns, wheat germs, rosemary, oregano, flavonoids, quercetin, phenolic benzyl amines. Furthermore, propyl gallate, octyl gallate, dodecyl gallate, butyl hydroxy anisole (BHA), butyl hydroxy toluole (BHT), lecithines, mono- and diglycerides of edible fatty acids esterified with citric acid, orthophosphates and Na-, K- and Ca-salts of monophosphoric acid and ascorbyl palmitate are suitable as antioxidants.

The W/O emulsions according to the present invention are suitable in particular for applying to food surfaces, wherein the food has preferably a water content of up to 10 wt. %, preferably up to 5 wt.-%. In a preferred embodiment, the W/O emulsion according to the present invention has a sufficiently low viscosity at application temperature, so that the application of W/O emulsion by spraying is possible. Preferred foods, to whose surface a W/O emulsion according to the present invention can be applied are, for example, cracker, chips (e.g. on the basis of potatoes, corn, cereal or bread), extruded snacks (snack) goods (e.g. flips) or leaching pastries (such as pretzel sticks). W/O emulsions according to the present invention are normally applied in an amount of 0.5 to 6 wt.-% to the food surfaces, based on the total weight of the food.

As already mentioned, an aspect of the present invention relates to the use of a compound of above formula (I) or (II) for creating, modifying or enhancing an Umami-taste.

Preferably, the compounds of formula (I) or (II) to be used according to the present invention (in a flavorfully effective amount) or the compositions according to the present invention are used in the (i) ready-to-use or ready-to-consume preparation or (ii) semi-finished goods used for nourishment or enjoyment, in particular in the sodium glutamate-reduced or sodium glutamate-free preparations used for nourishment or enjoyment.

The term "sodium glutamate-reduced" herein means that the preparation or semi-finished goods according to the present invention contains significantly less sodium glutamate than the conventional preparation or semi-finished goods, wherein the sodium glutamate content lies around 5 to <100 wt.-%, preferably 10 to 50 wt.-%, especially preferably 20 to 50 wt.-% below the sodium glutamate content of the conventional preparation. If, besides one or more compounds of formula (I) or (II) to be used according to the present invention, the preparation or semi-finished goods according to the invention contain sodium glutamate, the weight ratio of the total amount of compounds of formula (I) or (II) to sodium glutamate is preferably in the range of 1:1 to 1:200.

According to the present invention, the ready-to-use or ready-to-consume preparations used for nourishment or enjoyment contain one or more compounds of formula (I) or (II) to be used according to the present invention, preferably in an amount in the range of 0.01 ppm to 100 ppm, preferably in the range of 0.1 ppm to 50 ppm, in particular preferably in the range of 1 ppm to 30 ppm, based on the total weight of the ready-to-use or ready-to-consume preparation.

According to the present invention, the semi-finished goods used for nourishment or enjoyment contain one or more compounds of formula (I) or (II) to be used according to the present invention, preferably in an amount in the range of 10 ppm to 800 ppm, preferably in the range of 25 ppm to 750 ppm, in particular preferably in the range of 50 ppm to 700 ppm, based on the total weight of the semi-finished goods.

Sodium glutamate-reduced preparations according to the present invention, which comprise sodium glutamate, are particularly relevant, in which the amount of sodium glutamates is not sufficient, in order to be perceived as a satisfactory Umami-taste in a reference preparation which comprises no mixture according to the invention, but is otherwise identically composed (normal sodium glutamate-reduced preparation). And the amount of the mixture according to the invention is sufficient to achieve a satisfactory Umami taste impression.

The preparation used for nourishment or enjoyment in the sense of the invention are particularly baked goods (such as bread, dried biscuits, cakes, other cookies), beverages (such as vegetable juice, vegetable juice preparations), instant beverages (such as instant vegetable drinks), meat products (e.g. ham, fresh sausage preparations or raw sausage preparations, seasoned or marinated fresh or salt meat products), seasoned or marinated fish products (such as surimi), eggs or egg products (dried egg, egg white, egg yolk), cereal products (e.g. precooked finished rice products, rice flour products, millet and sorghum products, raw or precooked noodles and pasta products), milk products (e.g. fresh cheese, soft cheese, hard cheese, milk drinks, whey, butter, partially or completely hydrolyzed milk protein-containing products), products from soy protein or other soy beans-factions (such as soy milk and products made thereof, soya lecithin-containing preparations, fermented products like tofu or Tempe or products made thereof, soy sauce), vegetable preparations (such as ketchup, sauces, dried vegetables, frozen vegetables, precooked vegetables, vegetables pickled in vinegar, vegetable concentrates or vegetable paste, semi-boiled vegetables, potato preparations), snack (e.g. baked or fried potato chips or potato dough products, bread dough products, extrudates based on corn, rice or peanut), products based on fat and oil or emulsions of the same (e.g. mayonnaise, spread, remoulade, dressings, condiment preparations), other finished meals and soups (such as dry soups, instant soups, precooked soups), sauces (instant sauces, dry sauces, finished sauces), spices or spice preparations (e.g. mustard preparations, horseradish preparations), condiment mixtures and in particular seasonings, which is used for example, in the snack area.

(Sodium glutamate-reduced) sodium glutamate-containing semi-finished goods or the preparations used for nourishment or enjoyment are especially preferred, for example, baked goods (such as bread, dried biscuits, cakes, other cookies), vegetable juice preparations, meat products (e.g. ham, fresh sausage or raw sausage preparations, seasoned or marinated fresh meat products or salt meat products), seasoned or marinated fish products (such as surimi), eggs or egg products (dried egg, egg white, egg yolk), cereal products (e.g. precooked finished rice products, raw or precooked noodles and pasta products), milk products (e.g. fresh cheese, soft cheese, hard cheese, milk drinks, whey, butter, partially or completely hydrolyzed milk protein-containing products), products from soy protein or other soy beans-factions (such as soy milk and products made thereof, soya lecithin-containing preparations, fermented products like tofu or Tempe or products made thereof, soy sauce), fish sauces, for example anchovy sauces, oyster sauces, vegetables preparations (such as ketchup, sauces, dried vegetables, frozen vegetables, precooked vegetables, vegetables pickled in vinegar, semiboiled vegetables, potato preparations), snack (e.g. baked or fried potato chips or potato dough products, bread dough products, extrudates based on corn or peanut), products based on fat and oil or emulsions of the same (e.g. mayonnaise, spread, remoulade, dressings, condiment preparations), finished meals, soups (such as dry soups, instant soups, precooked soups), bouillon cube, sauces (instant sauces, dry sauces, finished sauces), spices, relish, condiment, condiment mixtures and particularly seasonings, which is used for example, in the snack area.

The preparations for the purposes of the invention can also be in the form of capsules, tablets (non-coated and coated tablets, such as enteric coatings), dragees, granules, pellets, solid mixtures, dispersions in liquid phases, emulsions, powder, solutions, paste or other swallowable or chewable preparations, for example, as a dietary supplement.

The semi-finished goods according to the invention normally serve for the preparation of the ready-to-use or ready-to-consume preparations used for nourishment or enjoyment.

According to the present invention, in particular, semi-finished goods used for nourishment or enjoyment can serve for additionally enhancing the Umami-taste of sodium glutamate-reduced foods and luxury foods, and also directly serve as condiment for industrial or non-industrial preparation of foods and/or luxury foods.

The semi-finished goods according to the invention contain compounds of formula (I) or (II) to be used according to the invention preferably in a total amount of 10 ppm to 800 ppm, preferably 25 ppm to 750 ppm, in particular, 50 ppm to 700 ppm,
and/or no sodium glutamate
and/or sodium glutamate in a proportion of 0.00001 to 10 wt.-%, preferably 0.0001 to 5 wt.-%, in particular 0.001 wt.-% to 2 wt.-%, (in each case alternatively no sodium glutamate),
and if necessary, a flavoring component in a proportion of 0.0001 wt.-% to 90 wt.-%, preferably 0.001 wt.-% to 30 wt.-%, in each case based on the total weight of semi-finished goods.

The preparations or semi-finished goods according to the present invention are preferably produced by dissolving the compounds of formula (I) or (II) to be used according to the invention in mixtures of ethanol and if necessary, demineralized and/or purified water and mixing, then converting the solutions into a (at least nearly) solid preparation by a drying process, preferably a spray drying, vacuum frozen drying, reverse osmosis, evaporation or other concentration process, or a combination of the above processes. The drying can be carried out with the aid of carrier substances (such as starch, starch derivates, maltodextrin, silica gel, see above) or auxiliary substances (e.g. vegetable gums, stabilizer). Preferably, the drying is carried out by spray drying or vacuum frozen drying.

Preferred preparations or semi-finished goods according to the present invention are relish, condiment mixture, condiment, bouillon cubes, instant soups, instant sauces, vegetarian finished meals, finished dishes containing meat, fish sauces such as anchovy sauces, oyster sauces and soy sauces.

According to another preferred embodiment of the present invention, in order to produce preparations or semi-finished goods according to the invention, the compounds of formula (I) or (II) to be used according to the invention and if necessary, other ingredients are firstly introduced into emulsions, into liposomes (e.g. based on phosphatidyl choline), into microspheres, into nanospheres or also into capsules, granules or extrudates from a matrix (e.g. from starch, starch derivates, cellulose and cellulose derivates such as hydroxypropyl cellulose, other polysaccharides such as alginate, natural fats, natural waxes such as beeswax or carnauba wax or from proteins like gelatine) for food and luxury food.

In another preferred method for preparation, the compounds of formula (I) or (II) to be used according to the invention are complexed with one or more suitable complexing agents, such as cyclodextrins or cyclodextrin derivates, preferably alpha- or betacyclodextrin, and used in this complex form.

The preparations according to the present invention, in which the matrix is selected so that the compounds of formula (I) or (II) to be used according to the invention are released from the matrix in delayed manner to achieve a long-lasting effect, are preferred. For example, natural fats, natural waxes (e.g. beeswax, carnauba wax), or also natural dietary fibers (wheat fibers, apple fibers, oat fibers, orange fibers) can herein be used as matrix.

Other ingredients of the ready-to-consume preparation or semi-finished goods used for nourishment or enjoyment according to the invention can be conventional basic materials, auxiliary materials and additives for food or luxury food, e.g., water, mixtures of fresh or processed, vegetable or animal basic materials or raw materials (such as raw, fried, dried, fermented, smoked and/or cooked meat, bone, cartilage, fish, vegetables, herbs, nuts, vegetable juices or vegetable pastes or their mixtures), digestible or indigestible carbohydrate (e.g. sucrose, maltose, fructose, glucose, dextrins, amylose, amylopectin, inulin, xylane, cellulose, tagatose), sugar alcohols (such as sorbitol, erythritol), natural or hardened fats (e.g. tallow, lard, palm oil, coconut oil, hardened vegetable fat), oils (such as sunflower oil, peanut oil, corn oil, olive oil, fish oil, soybean oil, sesame oil), fatty acids or their salts (e.g. potassium stearate), proteinogenic or non-proteinogenic amino acids and related compounds (e.g. gamma-aminobutyric acid, taurine), peptides (e.g., glutathione), native or processed proteins (such as gelatine), enzymes (e.g. peptidases), nucleic acids, nucleotides, taste modifier for unpleasant taste impressions, and other taste modulators for other, normally non-unpleasant taste impressions, other taste-modulating substances (e.g. inositol phosphate, nucleotides such as guanosine monophosphate, adenosine monophosphate, or other substances such as sodium glutamate or 2-phenoxypropionic acid), emulsifiers (for example, lecithins, diacylglycerols, gum arabic), stabilizers (e.g., carrageenan, alginate), preservatives (such as benzoic acid and its salts, sorbic acid and its salts), antioxidants (such as tocopherol, ascorbic acid), chelating agents (such as citric acid), organic or inorganic acidifier (such as acetic acid, phosphoric acid), additionally bitter substances (such as quinine, caffeine, limonin, amarogentin, humolone, lupolone, catechines, tannins), the enzymatic browning-prohibiting substances (e.g. sulphite, ascorbic acid), etheric oils, plant extracts, natural or synthetic dyestuffs or pigments (such as carotenoids, flavonoids, anthocyans, chlorophyll and their derivates), spices, trigeminally effective substances or plant extracts containing such trigeminally effective substances, synthetic, natural or natural-identical flavorings or odorous substances and odor modifier.

The compositions, preparations or semi-finished goods according to the present invention preferably contain a flavoring component, in order to round off and refine the taste and/or the smell. A composition according to the invention, which comprises a solid carrier sub-stance and a flavoring component as further ingredients, was already described above. Suitable flavoring components contain e.g. synthetic, natural or natural-identical flavorings, odorous substances and flavoring substances, reaction flavor, smoke flavor or other flavor-giving preparations (e.g. protein [partial-] hydrolysate, barbecue flavors, plant extracts, spices, spice preparations, vegetables and/or vegetable preparations), and suitable auxiliary substances and carrier substances. In particular, the flavoring components not according to the invention or their ingredients create a roast, fleshy (especially chicken, fish, marine animals, beef, pork, lamb, sheep, goat), vegetarian (particularly tomato, onion, garlic, celery, leeks, mushrooms, eggplant, seaweed), a spicy (in particular, black and white pepper, chili, pepper, cardamom, nutmeg, allspice, mustard and mustard products), fried, yeasty, boiled, greasy, salty and/or hot flavor impression, and thus can enhance the spicy impression. As a rule, the flavoring components contain more than one of said ingredients.

In another embodiment of the present invention, the compounds of formula (I) or (II) according to the present invention are used in the compositions, preparations and semi-finished goods according to the present invention, in combination with at least one (other, not in itself according to the invention) substance for masking or reducing an unpleasant (bitter, metallic, limy, sour, astringent) taste impression or to enhancing or producing a pleasant taste impression (sweet, salty, umami). In this way, an enhancement of taste, especially Umami-taste, can be achieved. These other substances can be selected from the following list, without limiting the invention with it: monosodium glutamate, glutamic acid, nucleotides (e.g. adenosine 5'-monophosphate, cytidine 5'-monophosphate, inosine 5'-monophosphate, guanosine 5-monophosphate) or its pharmaceutically acceptable salts, lactisole, hydroxyflavanones (e.g. eriodictyol, homoeriodictyol or their sodium salts), in particular in accordance with EP 1258200, hydroxybenzoic amides (for example, 2,4-dihydroxybenzoic acid vanillyl amide, 4-hydroxybenzoic acid vanillyl amide), mixtures of whey proteins with lecithinen, yeast extracts, plant hydrolysates, powdered vegetables (e.g. onion powder, tomato powder), plant extracts (e.g. lovage or mushrooms like shiitake), marine algae and mixtures of mineral salt.

Other favorable modulating flavorings and/or flavoring substances are preferably selected from the group consisting of 2,4-dihydroxybenzonic acid; 3-hydroxybenzonic acid; sodium salts, preferably sodium chloride, sodium lactate, sodium citrate, sodium acetate, sodium gluconoate; hydroxybenzonic amides, such as 2,4-dihydroxybenzonic acid-N-(4-hydroxy-3-methoxybenzyl)amide, 2,4,6-trihydroxybenzonic acid-N-(4-hydroxy-3-methoxybenzyl) amide, 2-hydroxy-benzonic acid-N-4-(hydroxy-3-methoxybenzyl)amide, 4-hydroxybenzonic acid-N-(4-hydroxy-3-methoxybenzyl)-amide, 2,4-dihydroxy benzonic acid-N-(4-hydroxy-3-methoxybenzyl)amide-monosodium salt, 2,4-dihydroxybenzonic acid-N-2-(4-hydroxy-3-methoxyphenyl)-ethyl-amide, 2,4-dihydroxybenzonic acid-N-(4-hydroxy-3-ethoxybenzyl)amide, 2,4-dihydroxybenzonic acid-N-(3,4-dihydroxybenzyl)amide and 2-hydroxy-5-methoxy-N-[2-(4-hydroxy-3-methoxyphenyl)ethyl]amide; (in particular those as described in WO 2006/024587 which includes the corresponding compounds disclosed therein, is incorporated into the present application for reference); hydroxydeoxybenzoins, such as 2-(4-hydroxy-3-methoxy-phenyl)-1-(2,4,6-trihydroxyphenyl)acetone, 1-(2,4-dihydroxyphenyl)-2-(4-hydroxy-3-methoxy-phenyl)acetone, 1-(2-hydroxy-4-methoxy phenyl)-2-(4-hydroxy-3-methoxy-phenyl)acetone (in particular those as described in WO 2006/106023 which includes the corresponding compounds disclosed therein, is incorporated into the present application for reference); hydroxyphenyl alkandionen, such as Gingerdion-[2], Gingerdion-[3], Gingerdion-[4], Dehydrogingerdion-[2], Dehydrogingerdion-[3], Dehydrogingerdion-[4]) (in particular those as described in WO 2007/003527 which includes the corresponding compounds disclosed therein, is incorporated into the present application for reference); Diacetyl-trimeren (in particular those as described in WO 2006/058893 which includes the corresponding compounds disclosed therein, is incorporated into the present application for reference); γ-aminobutyric acids (in particular those as described in WO 2005/096841 which includes the corresponding compounds disclosed therein, is incorporated into the present application for reference) and Divanillinen (in particular divanillin as described in WO 2004/078302 which includes the corresponding compounds disclosed therein, is incorporated into the present application for reference); bicyclo[4.1.0]heptane-7-carboxylic acid amide, in particular those as described in PCT/EP2007/061171 and the documents based on it (Symrise), which includes the corresponding compounds disclosed therein, is incorporated into the present application for reference.

In a preferred embodiment of the present invention, the compounds of formula (I) or (II) according to the invention are used in the compositions, preparations and semi-finished goods according to the present invention, in combination with at least one sweet-enhancing substance, especially with one or more compounds according to WO 2007/014879 A1 or WO 2007/107596 A1, especially with hesperetin and/or phloretin. The taste profile can be enhanced and deepened as well as rounded off by this way, especially in compositions, preparations and semi-finished goods with a spicy and/or salty taste. The total proportion of hesperetin and/or phloretin in such compositions or preparations is preferably in the range of 1 to 400 ppm, preferably in the range of 5-200 ppm, based on the total weight of the composition or preparation.

In addition to one or more sweet-enhancing substances, the compositions, preparations and semi-finished goods according to the invention can preferably contain flavoring substances, which cause a trigeminal stimulus (tingling, prickling, hot, cooling, etc.). Thus, a taste profile, which is further improved and preferred by consumers, was achieved by the combination of the compounds of formula (I) or (II) according to the present invention with hesperetin and/or phloretin on the one hand, and cis- and/or trans-pellitorin (see WO 2004/000787 or WO 2004/043906) on the other hand. The total proportion of cis- and/or trans-pellitorin in such compositions or preparations is preferably in the range of 0.5 to 500 ppm, preferably in the range of 5-100 ppm, based on the total weight of the composition or preparation.

As is known from the above text, another aspect of the present invention relates to a method for creating, modifying or enhancing a taste, especially an Umami-taste, in (i) a ready-to-use or ready-to-consume preparation or (ii) a semi-finished goods used for nourishment or enjoyment. Such a method according to the present invention comprises the following step:

Mixing a flavorfully effective amount of one or more compounds of formula (I) or (II), or a composition according to the invention with one or more other ingredients of (i) the ready-to-consume preparation or (ii) the semi-finished goods and/or
applying a flavorfully effective amount of one or more compounds of formula (I) or (II), or a composition according to the invention to one or more other ingredients of (i) the ready-to-consume preparation or (ii) the semi-finished goods and/or
embedding a flavorfully effective amount of one or more compounds of formula (I) or (II) or a composition according to the invention in a cladding material or matrix material.

According to the above-mentioned, another aspect of the present invention relates to a novel compound which falls within the general formula (I) and (II). Accordingly, one part of the invention is the compound of formula (I) or mixture of the compounds of formula (I)

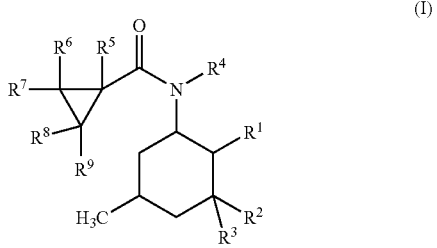

wherein:
$R^1, R^2, R^3$ in each case independently of each other represents hydrogen or an alkyl group having 1 to 3 C-atoms, in particular methyl, ethyl, n-propyl or iso-propyl, wherein at least one group is not H;
$R^4$ represents hydrogen, an alkyl group having 1 to 6 C-atoms, in particular methyl, ethyl, n-propyl, iso-propyl, n-butyl, iso-butyl, sec-butyl, tert-butyl, n-pentyl, 1-methyl-butyl, 2-methyl-butyl, 3-methyl-butyl, 1,2-dimethylpropyl, 1,1-dimethyl-propyl, 2,2-dimethyl-propyl, n-hexyl, 1-methyl-pentyl, 2-methyl-pentyl, 3-methyl-pentyl, 4-methyl-pentyl, 1-ethyl-butyl, 2-ethyl-butyl, 1,1-dimethyl-butyl, 1,2-dimethyl-butyl, 1,3-dimethyl -butyl, 2,2-dimethyl-butyl, 2,3-dimethyl-butyl, 3,3-dimethyl-butyl, 1-ethyl-1-methyl-propyl, 1-ethyl-2-methyl-propyl, 1,1,2-trimethyl-propyl or 1,2,2-trimethyl-propyl, or an alkenyl group having 2 to 6 C-atoms, in particular 1-propenyl, 2-propenyl, 1-methyl-1-propenyl, 2-methyl-1-propenyl or 2-methyl-2-propenyl;
$R^5, R^6, R^7, R^8$ in each case independently of each other represents hydrogen or methyl;
$R^9$ represents hydrogen, an alkyl group having 4 to 12 C-atoms, in particular n-butyl, iso-butyl, sec-butyl, tert-butyl, n-pentyl, 1-methyl-butyl, 2-methyl-butyl, 3-methyl-butyl, 1,2-dimethyl-propyl, 1,1-dimethyl-propyl, 2,2-dimethyl-propyl, n-hexyl, 1-methyl-pentyl, 2-methyl-pentyl, 3-methylpentyl, 4-methyl-pentyl, 1-ethyl-butyl, 2-ethyl-butyl, 1,1-dimethyl-butyl, 1,2-dimethyl-butyl, 1,3-dimethyl-butyl, 2,2-dimethyl-butyl, 2,3-dimethylbutyl, 3,3-dimethylbutyl, 1-ethyl-1-methyl-propyl, 1-ethyl-2-methylpropyl, 1,1,2-trimethyl-propyl, 1,2,2-trimethyl-propyl, n-heptyl, n-octyl, n-nonyl, n-decyl, n-undecyl or n-dodecyl or an alkenyl group having 4 to 12 C-atoms, in particular 1-methyl-1-propenyl, 2-methyl-1-propenyl or 2-methyl-2-propenyl,
with the proviso that the compounds of formula (I), which fall within the formula (III), is excluded.

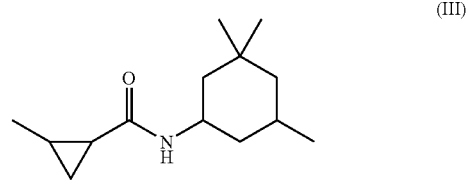

Compounds of formula (III)—in other connection—have already been known from the prior art (see above) and is naturally excluded accordingly.

In view of the applicant, the publication text of WO 2004/056745 does not sufficiently disclose the compounds which fall within the general formula I. If contrary to this view, however, specific compounds, which fall within the general formula I as defined above, are to be considered as disclosed in said publication text. These are naturally not to be understood as a part of the invention. Accordingly, WO 2004/056745 is incorporated into this application for concretion. This in particular also applies to claims 1 and 2 in said publication text. It is precautionarily preferred that all compounds, which are to be considered as disclosed in WO 2004/056745, are not the subject of the present invention.

Preferably, the compounds of formula (I) according to the present invention, in which a compound or the compounds of formula (I) is a compound or are compounds selected from the group consisting of:
(1R,3S)-2,2-dimethyl-3-(2-methyl-propenyl) -cyclopropanecarboxylic acid-((1S,2S,5R)-2-isopropyl-5-methyl-cyclohexyl)-amide, (1R,3S)-2,2-dimethyl-3-(2-methyl-propenyl)cyclopropanecarboxylic acid-((1R,2R,5S)-2-isopropyl-5-methyl-cyclohexyl)-amide, (1S,3R)-2,2-dimethyl-3-(2-methyl-propenyl)-cyclopropanecarboxylic acid-((1S,2S,5R)-2-isopropyl-5-methyl-cyclohexyl)-amide, (1S,3R)-2,2-dimethyl-3-(2-methyl-propenyl)cyclopropanecarboxylic acid-((1R,2R,5S)-2-isopropyl-5-methyl-cyclohexyl)-amide, (1S,3S)-2,2-dimethyl-3-(2-methyl-propenyl)-cyclopropanecarboxylic acid-((1S,2S,5R)-2-isopropyl-5-methyl-cyclohexyl)-amide, (1S,3S)-2,2-dimethyl-3-(2-methyl-propenyl) cyclopropanecarboxylic acid-((1R,2R,5S)-2-isopropyl-5-methyl-cyclohexyl)-amide, (1R,3R)-2,2-dimethyl-3-(2-methyl-propenyl)-cyclopropanecarboxylic acid-((1S,2S,5R)-2-isopropyl-5-methyl-cyclohexyl)-amide, (1R,3R)-2,2-dimethyl-3-(2-methyl-propenyl) cyclopropanecarboxylic acid-((1R,2R,5S)-2-isopropyl-5-methyl-cyclohexyl)-amide, Preferred compounds according to the invention or mixture of the compounds according to the invention are those, which are a compound or compounds of formula (II)

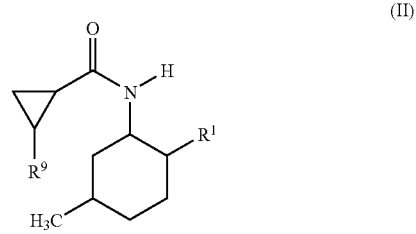

and wherein:

$R^1$ represents an alkyl group having 1 to 3 C-atoms, especially methyl, ethyl, n-propyl or i-propyl.

$R^9$ represents hydrogen, an alkyl group having 4 to 12 C-atoms, especially n-butyl, iso-butyl, sec-butyl, tert-butyl, n-pentyl, 1-methyl-butyl, 2-methylbutyl, 3-methyl-butyl, 1,2-dimethyl-propyl, 1,1-dimethyl-propyl, 2,2-dimethyl-propyl, n-hexyl, 1-methyl-pentyl, 2-methyl-pentyl, 3-methylpentyl, 4-methyl-pentyl, 1-ethyl-butyl, 2-ethyl-butyl, 1,1-dimethyl-butyl, 1,2-dimethyl-butyl, 1,3-dimethyl-butyl, 2,2-dimethyl-butyl, 2,3-dimethylbutyl, 3,3-dimethyl-butyl, 1-ethyl-1-methyl-propyl, 1-ethyl-2-methylpropyl, 1,1,2-trimethyl-propyl, 1,2,2-trimethyl-propyl, n-heptyl, n-octyl, n-nonyl, n-decyl, n-undecyl or n-dodecyl or an alkenyl group having 4 to 12 C-atoms, especially methyl-1-propenyl, 2-methyl-1-propenyl or 2-methyl-2-propenyl.

The compounds or mixtures of compounds of general formula (II) as above defined, which are selected from the group consisting of:

Cyclopropanecarboxylic acid-((1R,2S,5R)-2-isopropyl-5-methyl-cyclohexyl)-amide, cyclopropanecarboxylic acid-((1S,2R,5S)-2-isopropyl-5-methyl-cyclohexyl)-amide, cyclopropanecarboxylic acid-((1S,2S,5R)-2-isopropyl-5-methyl-cyclohexyl)-amide, cyclopropanecarboxylic acid-((1R,2R,5S)-2-isopropyl-5-methyl-cyclohexyl)-amide, cyclopropanecarboxylic acid-((1R,2R,5R)-2-isopropyl-5-methyl-cyclohexyl)-amide, cyclopropanecarboxylic acid-((1S,2S,5S)-2-isopropyl-5-methyl-cyclohexyl)-amide, cyclopropanecarboxylic acid-((1S,2R,5R)-2-isopropyl-5-methyl-cyclohexyl)-amide and cyclopropanecarboxylic acid-((1R,2S,5S)-2-isopropyl-5-methyl-cyclohexyl)-amide, are particularly preferred according to the present invention.

The present invention further relates to a method for preparing a compound of formula (11) and/or (12) or a mixture of formula (11) and/or (12), comprising the following steps:

(a) carrying out a Leuckart-Wallach reaction (see for example Ann. Chem. 1893, 276, 296-313) starting from enantiomerically pure or racemic menthone to obtain a corresponding formamides of formula (III),

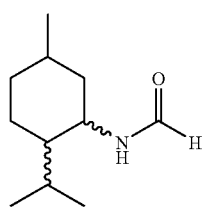

(III)

(b) carrying out a fractional crystallization of the corresponding neo-menthyl form amides, preferably in a diastereomeric purity≧90 wt.-%, preferably ≧95 wt.-% (racemic or in the respective D- or L-form formula (IV) and (V)),

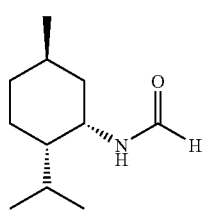

(IV)

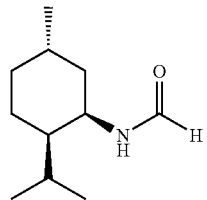

(V)

(c) saponifying the neo-menthyl formamides with a strong acid, preferably a mineral acid, in particular hydrochloric acid or sulfuric acid, with diastereomeric purity≧90%, preferably ≧95% (racemic or in the respective D- or L-form formula (VI) and (VII)), and

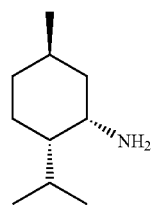

(VI)

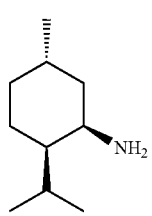

(VII)

(d) reacting the amine either with (i) cyclopropanecarboxylic acid chloride, preferably under Schotten-Baumann condition or with (ii) cyclopropanecarboxylic acid, preferably under catalysis of boric acid (see Organic Process Research & Development 2007, 11, 1065-1068), wherein diastereomeric purity preferably ≧90%, preferably ≧95% (racemic or in the respective D- or L-form), to obtain (11) and/or (12)

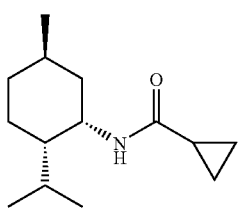

(11)

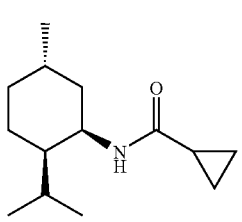

(12)

Hereinafter, the invention is now explained in more detail on the basis of examples. Other aspects of the present invention can be derived from the attached claims.

DESCRIPTION OF FIGURES

FIG. 1: Taste comparison of a 1:1 mixture of cyclopropanecarboxylic acid-((1S,2S,5R)-2-isopropyl-5-methyl-cyclohexyl)amide (11) and cyclopropanecarboxylic acid-((1R,2R,5S)-2-isopropyl-5-methyl-cyclohexyl)amide (12) with sodium glutamate.

With the aid of tasting by a panel of trained subjects, the taste of a 0.5% American beef extract as base (light grey line) was compared with the taste of firstly, such a base, to which 5 ppm of mixture consisting of cyclopropanecarboxylic acid-((1S,2S,5R)-2-isopropyl-5-methyl-cyclohexyl)amide (11) and cyclopropanecarboxylic acid-((1R,2R,5S)-2-isopropyl-5-methyl-cyclohexyl)amide (12) was added (solid line), and secondly such a base, to which 0.05 wt.-% of MSG was added (broken line).

The subjects rated the strength of the stated trend of taste by ranking of scores on a scale from 0 (no corresponding taste) to 6 (very strong corresponding taste). The average values of respective scores are illustrated.

EXAMPLES

The following examples illustrate the present invention without limiting it. All %-data refer to wt-%, unless otherwise specifically noted.

According to the procedure of Wallach et al. (Ann. Chem. 1893, 276, 296-313), menthyl amines used as starting material are prepared from the corresponding menthone with a purity of ≧90%, preferably ≧95%. A mixture of all possible isomeric menthyl amines can be obtained according to the above-mentioned procedure without corresponding crystallization of menthyl formamides (an intermediate product) in a purity of 99.3 wt.-% (24.1% menthyl amine, 55.5% neo-menthyl amine, 2.4% iso-menthyl amine, 17.3% neoiso-menthyl amine). When doing so, not only enantiomerically pure D- or L-menthones but also a racemic D/L-menthone mixture can be used. All used menthones can be mixed with up to 25% of the corresponding iso-menthones.

Individual enantiomerically pure and diastereomerically pure menthyl amines can be pre-pared by conversion of the corresponding menthol into azide (Synthesis 1999, 8, 1373) and subsequent reduction with LiAlH4 (J. Am. Chem. Soc. 1962, 2925), see AAV1

General Preparation Procedure (AAV1): Amines Starting From Alcohols (a) Preparation of chlormesylates: 30-35 mmol of the corresponding alcohol are dissolved in 50 ml of pyridine in a 100 ml round flask and cooled down to 0° C. Then, 1.1-1.5 mmol of chlormethane sulfonyl chloride are dropwise slowly added and the mixture is stirred for further 20 minutes at 0° C. Then the mixture is diluted with diethyl ether and water. The etheric phase is separated and subsequently washed with water, 10% HCl solution, saturated sodium carbonate solution and saturated saline solution. After drying over sodium sulfate and removing the solvent under vacuum, the product is purified by either column chromatography (diethyl ether/pentane=1:4), or further reacted directly.

(b) Preparation of azide: The corresponding Chlormesylate is added into 0.5-1.5 mL/mmol of DMF, and mixed with 2.0-3.0 equivalents of sodium azide, and the mixture is heated at 90° C. for 1 to 2 h. After cooling down to RT, the mixture is diluted with diethyl ether and water, and the organic phase is washed with water and saturated saline solution. After drying over sodium sulfate, the product is concentrated in the rotary evaporator and purified with column chromatography (diethyl/pentane=1:4).

(c) Reduction to amines: The corresponding azide is added into 0.5-1.5 ml/mmol of diethyl ether, and then dropwise slowly added to a suspension of 1.0-2.0 equivalent of lithium aluminium in 2.0 mL/mmol of diethyl ether. After refluxing for 1 h under reflux, the reaction mixture is mixed with 10% sodium hydroxide solution till production of a white precipitate. After the addition of sodium sulfate, the reaction mixture is filtered and the solvent is removed in the rotary evaporator. The residue is dissolved in 10% hydrochloric acid and washed with diethyl ether. Then the aqueous phase is basically adjusted with potassium carbonate and also extracted with diethyl ether. After drying over sodium sulfate, the corresponding amines as enantiomerically pure/diastereomerically pure compound are obtained after the solvent is removed in the rotary evaporator.

General Preparation Procedure (AAV2): Reaction with Acid Chlorides 1.1-1.5 equivalents of the corresponding acid chloride are dropwise slowly added into the solution of corresponding amine and 2.0-3.5 equivalents of triethyl amine in DMC. The mixture is heated up to RT and stirred for 4 h, then diluted with dichloromethane and washed with 10% hydrochloric acid and saturated sodium bicarbonate solution. After drying over sodium sulfate and subsequent removal of the solvent, the purification are carried out by recrystallisation or chromatography.

Synthesis Example 1

Cyclopropanecarboxylic acid ((1S,2S,5R)-2-isopropyl-5-methylcyclohexyl)-amide (11)

Enantiomerically pure (L)-neo-menthyl amine was obtained from enantiomerically pure (L)-menthol by reaction analogous to AAV 1. Then the said amine was converted into said product with cyclopropanecarboxylic acid chloride according to AAV 2. The purification of the products was carried out by crystallization (pentane/dichloromethane).

Analysis data:

$^1$H-NMR (400 MHz, CDCl$_3$): 0.71 (m, 2H); 0.86-092 (m, 9H); 0.93-1.09 (m, 5H); 1.28-1.40 (m, 2H); 1.47 (m, 1H); 1.75 (m, 1H); 1.82-1.89 (m, 2H); 4.37 (m, 1H); 5.63 (bd, J=8.4 Hz, 1H) ppm.

$^{13}$C-NMR (100 MHz, CDCl$_3$): 6.9 (CH$_2$); 15.9 (CH); 20.9 (CH$_3$); 21.0 (CH$_3$); 22.3 (CH$_3$); 25.5 (CH$_2$); 26.9 (CH); 29.6 (CH); 34.8 (CH$_2$); 40.2 (CH2); 46.1 (CH); 46.3 (CH); 172.5 (C=O) ppm.

Mass spectrum (EI): m/z (%)=223 (M$^+$, 13); 180 (14); 138 (55); 112 (22); 99 (12); 98 (19) 95 (21); 86 (100); 81 (14); 70 (61); 69 (50); 55 (18); 43 (18); 41 (42).

Synthesis Example 2

Cyclopropanecarboxylic acid((1R,2R,5S)-2-isopropyl-5-methylcyclohexyl)-amide (12)

Enantiomerically pure (D)-neo-menthyl amine was obtained from enantiomerically pure (D)-menthol by reaction analogous to AAV 1, then the said amine was converted into said product with Cyclopropanecarboxylic acid chloride. The purification of the product was carried out by crystallization (pentane/dichloromethane).

Analysis data:

$^1$H-NMR (400 MHz, CDCl$_3$): 0.71 (m, 2H); 0.87-0.91 (m, 9H); 0.93-1.09 (m, 5H); 1.28-1.41 (m, 2H); 1.47 (m, 1H); 1.75 (m, 1H); 1.82-1.89 (m, 2H); 4.38 (m, 1H); 5.61 (bd, J≈8 Hz, 1H) ppm.

¹³C-NMR (100 MHz, CDCl₃): 6.9 (CH₂); 15.1 (CH); 20.9 (CH₃); 21.0 (CH₃); 22.3 (CH₃); 25.5 (CH₂); 26.9 (CH); 29.6 (CH); 34.8 (CH₂); 40.2 (CH2); 46.1 (CH); 46.3 (CH); 172.5 (C=O) ppm.

Mass spectrum (EI): m/z (%)=223 (M⁺, 13); 180 (16); 138 (59); 112 (28); 99 (14); 98 (23); 86 (100); 81 (17); 70 (85); 69 (71); 55 (20); 43 (28); 41 (67); 39 (14).

Synthesis Example 3

Cyclopropanecarboxylic acid cyclohexyl amide (not according to the invention) The said product was obtained from cyclohexyl amine by reaction with cyclopropanecarboxylic acid chloride analogous to AAV 2. The purification of products was carried out by crystallization (Hexane/Acetone).

Analysis dates:
¹H-NMR (400 MHz, CDCl₃): 0.70 (m, 2H); 0.94 (m, 2H); 1.08-1.22 (m, 3H); 1.28-1.41 (m, 3H); 1.61 (m, 1H); 1.71 (m, 2H); 1.92 (m, 2H); 3.77 (m, 1H); 5.74 (bs, 1H) ppm.
¹³C-NMR (100 MHz, CDCl₃): 6.9 (CH₂); 14.8 (CH); 25.0 (CH₂); 25.6 (CH₂); 33.3 (CH₂); 48.3 (CH); 172.6 (C=O) ppm.

Mass spectrum (EI): m/z (%)=167 (M⁺, 9); 124 (20); 99 (15); 98 (26); 86 (100); 72 (21); 70 (15); 69 (90); 67 (11); 56 (66); 55 (19); 44 (11); 43 (34); 41 (62); 39 (24).

Synthesis Example 4A (Schotten-Baumann variant): Cyclopropanecarboxylic acid ((1S,2S,5R)-2-isopropyl-5-methyl-cyclohexyl)-amide (11)/Cyclopropanecarboxylic acid-((1R,2R,5S)-2-isopropyl-5-methyl-cyclohexyl)-amide (12)

(D/L)-neo-menthyl amine was provided in a mixture of 1.1 equivalent of 3 wt.-% sodium hydroxide solution and 0.5-1.0 ml/mmol of acetone at room temperature, and was mixed with 1.0 equivalent of cyclopropanecarboxylic acid chloride using spraying pump. The mixture was heated up to 50° C. after the addition was completed (the product has already partially participated), by doing so, the solid was again dissolved in solution. Now the mixture was mixed with 2.5-3.0 ml/mmol of tap water and cooled down to 5° C. The solid was removed by filtration and thoroughly washed with phosphate buffer, before the product was dried in drying oven at 65° C. till mass constancy.

The NMR and MS-data correspond to those of synthesis example 1 and 2.

Synthesis Example 4B (boric acid catalysis): Cyclopropanecarboxylic acid ((1S,2S,5R)-2-isopropyl-5-methyl-cyclohexyl)-amide (11)/Cyclopropanecarboxylic acid-((1R,2R,5S)-2-isopropyl-5-methyl-cyclohexyl)-amide (12)

Cyclopropanecarboxylic acid was dissolved in 1.5-2.5 ml/mmol of toluene at room temperature and mixed with 0.1 equivalent of boric acid as well as 1.05 equivalent of (D/L)-neo-menthyl amine. Now, the reaction mixture was heated in water separator to reflux. If no water came out any more and the reaction was finished (approx. 16 h), the reaction mixture was diluted with further 1.5-2.5 ml/mmol of toluene and cooled down to room temperature. Then the mixture was washed using 10% hydrochloric acid, tap water and saturated sodium bicarbonate solution. After drying over sodium sulfate, the toluene was removed by distillation and the residue was suspended in pentane. The solid was removed by filtration and washed with pentane several times, and then dried at 40° C. under vacuum.

The NMR and MS-data correspond to those of synthesis example 1 and 2.

A mixture of cyclopropanecarboxylic acid ((1S,2S,5R)-2-isopropyl-5-methyl-cyclohexyl)amide (11) and cyclopropanecarboxylic acid-((1R,2R,5S)-2-isopropyl-5-methyl-cyclohexyl)amide (12) are used in the following examples, as it can be obtained according to example 4A. Since it is herein a racemate, the weight ratio of (11):(12) is 1:1.

Example 1

Spray-dried Composition for Creating an Umami-taste

| 1.1 | Ingredient | proportion |
|---|---|---|
| | Mixture of 11.2% cyclopropanecarboxylic acid((1R,2S,5R)-2-isopropyl-5-methyl-cyclohexyl)-amide (9), 11.2% cyclopropanecarboxylic acid((1S,2R,5S)-2-isopropyl-5-methyl-cyclohexyl)-amide (10), 31.4% cyclopropanecarboxylic acid((1S,2S,5R)-2-isopropyl-5-methyl-cyclohexyl)-amide (11), 31.4% cyclopropanecarboxylic acid((1R,2R,5S)-2-isopropyl-5-methyl-cyclohexyl)-amide (12), 0.6% cyclopropanecarboxylic acid((1R,2R,5R)-2-isopropyl-5-methyl-cyclohexyl)-amide (13), 0.6% cyclopropanecarboxylic acid((1S,2S,5S)-2-isopropyl-5-methyl-cyclohexyl)-amide (14), 6.8% cyclopropanecarboxylic acid((1S,2R,5R)-2-isopropyl-5-methyl-cyclohexyl)-amide (15) and 6.8% cyclopropanecarboxylic acid((1R,2S,5S)-2-isopropyl-5-methyl-cyclohexyl)-amide (16) | 2 g |
| | Maltodextrin | 98 g |

| 1.2 | Ingredient | proportion |
|---|---|---|
| | Mixture of cyclopropanecarboxylic acid ((1S,2S,5R)-2-isopropyl-5-methyl-cyclohexyl)-amide (11)/cyclopropanecarboxylic acid((1R,2R,5S)-2-isopropyl-5-methyl-cyclohexyl)-amide (12) (1:1) | 4 g |
| | Maltodextrin | 96 g |

The ingredients were dissolved in a mixture of ethanol and demineralized water, and then spray-dried.

Example 2

Flavoring Composition

| Component | proportion |
| --- | --- |
| 10 wt.-% Pellitorin in 1,2-propylene glycol/diethyl malonate (1:1) | 0.25 g |
| Mixture of Cyclopropanecarboxylic acid ((1S,2S,5R)-2-isopropyl-5-methyl-cyclohexyl)-amide (11)/Cyclopropanecarboxylic acid((1R,2R,5S)-2-isopropyl-5-methyl-cyclohexyl)-amide (12) | 10.00 g |
| Hesperetin | 2.00 g |
| Phloretin | 1.50 g |
| Propylene glycol | 86.25 g |

The components (substances and/or solutions) were mixed in above-mentioned quantity proportion, and then introduced into propylene glycol and thoroughly dissolved by slightly heating.

Example 3

Condiment Containing Compound for Creating an Umami-taste and a Flavoring Composition

| part | Ingredient | Content |
| --- | --- | --- |
| A | (1:1)-Mixture of (11) + (12) | 0.02 g |
|   | Sodium chloride | 15.0 g |
| B | Mustard seed flour | 5.0 g |
|   | Mustard flavor | 0.1 g |

Part A was weighted. 290 ml of water was provided and part A was added under agitation and dissolved. The solution was diluted with water to 1.84 kg (pH 6.0) and then freeze-dried (eutectic point: −15° C.; working vacuum: 0.52 mbar; adjusting surface temperature: −5° C. to +25° C.). The product was mixed with mustard seed flour and mustard flavor from part B, and converted into a condiment.

Example 4

Instant Soup, Type Leek Cream

| Ingredient | Reference preparation A | preparation B according to the invention | preparation C according to the invention | preparation D according to the invention |
| --- | --- | --- | --- | --- |
| Potato starch | 20.0 g | 21.0 g | 21.0 g | 21.0 g |
| Fat powder | 25.0 g | 26.0 g | 26.0 g | 26.0 g |
| Lactose | 20.0 g | 21.0 g | 21.0 g | 21.0 g |
| Maltodextrin | 11.73 g | 11.727 g | 11.70 g | 11.43 g |
| Cooking salt | 8.0 g | 8.0 g | 8.0 g | 8.0 g |
| Sodium glutamate | 3.0 g | — | — | — |
| Spinach powder | 2.0 g | 2.0 g | 2.0 g | 2.0 g |
| Green leek powder | 2.0 g | 2.0 g | 2.0 g | 2.0 g |
| Citric acid, as powder | 0.3 g | 0.3 g | 0.3 g | 0.3 g |
| Harded vegetable fat | 3.0 g | 3.0 g | 3.0 g | 3.0 g |
| Freeze-dried leek | 1.0 g | 1.0 g | 1.0 g | 1.0 g |
| Chicken flavor | 1.0 g | 1.0 g | 1.0 g | 1.0 g |
| Condiment mixture, type "green leek", powder | 2.0 g | 2.0 g | 2.0 g | 2.0 g |
| Condiment mixture, type "cooked onion" | 0.6 g | 0.6 g | 0.6 g | 0.6 g |
| Yeast-condiment mixture, type "vegetable stock", powder | 0.3 g | 0.3 g | 0.3 g | 0.3 g |
| *Curcuma*-extract | 0.07 g | 0.07 g | 0.07 g | 0.07 g |
| (1:1)-mixture of (11) + (12) | — | 0.006 g | 0.06 g | 0.60 g |

5 g of respective powder mixture was infused with each 100 ml of hot water, in order to obtain a ready-to-consume soup.

With tasting by a panel of trained subjects, the reference preparation A and the preparation C according to the invention were equally rated. As for the preparation B according to the invention, Umami-taste (and mouthfulness) was described as perceivable, however, weaker, as compared with preparations A and C. The preparation D according to the invention was rated as very distinctive and considerably stronger than the preparations A and C as to Umami-taste (and mouthfulness).

Example 5

Instant Soup, Type Chicken Soup with Noodle

| Ingredient | Reference preparation A | preparation B according to the invention | preparation C according to the invention | preparation D according to the invention |
|---|---|---|---|---|
| Starch | 16 g | 17.2 g | 17.2 g | 17.2 g |
| Cooking salt | 7 g | 7 g | 7 g | 7 g |
| Saccharose, refined | 3.2 g | 3.2 g | 3.2 g | 3.2 g |
| Sodium glutamate | 3.2 g | — | — | — |
| Sodium inosinate/sodium guanylate in proportion of 1:1 | 0.8 g | 0.8 g | 0.8 g | 0.8 g |
| Acidicly hydrolyzed vegetable protein | 8.0 g | 8.0 g | 8.0 g | 8.0 g |
| Fat powder | 2.0 g | 2.0 g | 2.0 g | 2.0 g |
| Vegetable fat, spray dried | 1.0 g | 1.0 g | 1.0 g | 1.0 g |
| Freeze-dried chicken meet, in small pieces | 2.0 g | 2.0 g | 2.0 g | 2.0 g |
| Soup noodle | 32.0 g | 33.0 g | 33.0 g | 33.0 g |
| Maltodextrin | 12.16 g | 13.157 g | 13.13 g | 12.86 g |
| Chinese vegetable, freeze dried | 4.6 g | 4.6 g | 4.6 g | 4.6 g |
| Chicken flavor | 8.0 g | 8.0 g | 8.0 g | 8.0 g |
| Food coloring riboflavin | 0.04 g | 0.04 g | 0.04 g | 0.04 g |
| (1:1)-mixture of (11) + (12) | — | 0.006 g | 0.06 g | — |
| Flavoring composition according to A | — | — | — | 0.60 g |

4.6 g of respective powder mixture were cooked in each 100 ml of water for 10 minutes, in order to obtain a ready-to-consume soup.

With tasting by a panel of trained subjects, the reference preparation A and the preparation C according to the invention were equally rated. As for the preparation B according to the invention, Umami-taste (and mouthfulness) was described as perceivable, however, weaker, as compared with preparations A and C. The preparation D according to the invention was rated as very distinctive and considerably stronger than the preparations A and C as to Umami-taste (and mouthfulness).

Example 6

Condiment Mixture, Type "Pepper"

| Ingredient | Reference preparation A | preparation B according to the invention | preparation C according to the invention | preparation D according to the invention |
|---|---|---|---|---|
| Milk protein | 0.8 g | 0.8 g | 0.8 g | 0.8 g |
| Locust bean kernel flour | 2.0 g | 2.0 g | 2.0 g | 2.0 g |
| Corn starch | 25.0 g | 26.994 g | 26.94 g | 26.4 g |
| Cooking salt | 14.0 g | 15.0 g | 15.0 g | 15.0 g |
| Paprika powder | 12.0 g | 13.0 g | 13.0 g | 13.0 g |
| Tomato powder | 12.0 g | 13.0 g | 13.0 g | 13.0 g |
| Saccharose | 4.0 g | 4.0 g | 4.0 g | 4.0 g |
| Garlic powder | 0.5 g | 0.5 g | 0.5 g | 0.5 g |
| Harded vegetable fat | 8.0 g | 8.0 g | 8.0 g | 8.0 g |
| Fat powder | 11.0 g | 11.0 g | 11.0 g | 11.0 g |
| Sodium glutamate | 6.0 g | — | — | — |
| Food coloring beetroot and paprika | 2.0 g | 2.0 g | 2.0 g | 2.0 g |
| Flavor Type "Pepper" | 2.0 g | 2.0 g | 2.0 g | 2.0 g |
| Flavor Type "Pizza" | 1.2 g | 1.2 g | 1.2 g | 1.2 g |
| Flavour Type "Tomato" | 0.4 g | 0.4 g | 0.4 g | 0.4 g |
| Extract from black pepper | 0.1 g | 0.1 g | 0.1 g | 0.1 g |
| (1:1)-mixture of (11) + (12) | — | 0.012 g | 0.12 g | 1.20 g |

In each case 100 g of pig nape steak were bestewed uniformly with in each case 1.7 g of preparation A, B, C and D and roasted. With tasting by a panel of trained subjects, the reference preparation A and the preparation C according to the invention were equally rated. As for preparation B according to the invention, Umami-taste (and mouthfulness) were described as perceivable, however, weaker, as compared with preparations A and C. The preparation D according to the invention was rated as very distinctive and considerably stronger than the preparations A and C as to Umami-taste (and mouthfulness).

Example 7

Tomato Ketchup

| Ingredient | Reference preparation A | preparation B according to the invention | preparation C according to the invention | preparation D according to the invention |
|---|---|---|---|---|
| Sodium glutamate | 6 g | — | — | — |
| Cooking salt | 2 g | 2 g | 2 g | 2 g |
| Starch, Farinex WM 55 | 1 g | 1 g | 1 g | 1 g |
| Sucrose | 12 g | 12 g | 12 g | 8.4 g |
| Tomato-concentrate 2-fold | 36 g | 36 g | 36 g | 32 g |
| Glucose sirup 80 Brix | 18 g | 18 g | 18 g | 18 g |
| Spirits vinegar 10% | 7 g | 7 g | 7 g | 3 g |
| Water | 18 g | 23.8 g | 23.5 g | 34.7 g |
| Phloretin 2.5% in 1,2-propylene glycol | — | — | — | 0.2 g |
| Hesperetin 2.5% in 1,2-propylene glycol | — | — | — | 0.2 g |
| (1:1)-mixture of (11) + (12) | — | 0.2 g | 0.5 g | 0.5 g |

The components were mixed in given order and the finished ketchup were homogenized by means of a stirring unit, filled into bottles and sterilized.

Example 8

Bouillon

| Ingredient | Reference preparation A | Sodium glutamate-reduced reference preparation B | Sodium glutamate-reduced preparation C according to the invention | Sodium glutamate-free preparation D according to the invention |
|---|---|---|---|---|
| Fat powder | 8.77 g | 8.77 g | 8.77 g | 8.77 g |
| Sodium glutamate | 8.77 g | 5 g | 5 g | — |
| Yeast extract powder | 12.28 g | 12.28 g | 12.28 g | 12.28 g |
| Cooking salt | 29.83 g | 29.83 g | 29.83 g | 29.83 g |
| Maltodextrin | 37.28 g | 37.28 g | 37.28 g | 37.28 g |
| Natural vegetable extract | 3.07 g | 3.07 g | 3.07 g | 3.07 g |
| (1:1)-mixture of (11) + (12) | — | — | 0.10 g | 0.24 g |

15 g of respective powder mixture was infused with each 1000 ml of hot water. With tasting by a panel of trained subjects, the reference preparation A and the sodium glutamate-free preparation D according to the invention were equally rated. As for the preparation C according to the invention, a considerable improvement regarding Umami-taste (and mouthfulness) was likewise observed, compared with the sodium glutamate-reduced reference preparation B.

Example 9

Reaction Flavor

| component | application [in gram] |
|---|---|
| L-Alanine | 41.0 |
| L-Aspartic acid | 123.0 |
| Succinic acid | 4.7 |
| Calcium chloride dihydrate | 7.0 |
| L-Cysteine•HCl monohydrate | 11.0 |
| Dipotassium phosphate | 6.0 |
| Fructose ground | 1.0 |
| L-Isoleucine | 1.6 |
| Potassium chloride | 228.0 |
| L-Leucine | 1.6 |
| L-Lysine•HCl | 3.6 |
| Magnesium chloride hexahydrate | 19.0 |
| Maltodextrin | 49.0 |
| L-Phenylalanine | 2.0 |
| L-Proline | 74.0 |
| L-Serine | 6.5 |
| L-Threonine | 3.0 |
| L-Valine | 9.0 |
| Water | 399.0 |
| (1:1)-mixture of (11) + (12), 20 wt.-% in EtOH | 10.0 |

All components were mixed at 40° C. and then heated at 85° C. for 10 minutes (reflux reaction). After the mixture was cooled down to 40° C., it was adjusted using caustic potash solution to pH 5. This Umami-reaction flavor instead of (1:1)-mixture of (11)+(12) of Example 5 was analogously incorporated into the Bouillon—preparations C and D of application Example 5 respectively, in doing so, 12 g of Umami-reaction flavor was used in preparation C and 28 g of Umami-reaction flavor were used in preparation D.

Example 10

Condiment Mixture for Potato Chips

| Ingredient | Reference preparation A | Sodium glutamate-reduced reference preparation B | Sodium glutamate-reduced preparation C according to the invention | Sodium glutamate-free preparation D according to the invention |
|---|---|---|---|---|
| Sodium glutamate | 3.50 g | 2 g | 2 g | — |
| Cheese powder | 10.00 g | 10.00 g | 10.00 g | 10.00 g |
| Garlic powder | 2.00 g | 2.00 g | 2.00 g | 2.00 g |
| Whey powder | 38.86 g | 38.86 g | 38.86 g | 38.86 g |
| Condiment extract oil | 0.20 g | 0.20 g | 0.20 g | 0.20 g |
| Paprika powder | 9.80 g | 9.80 g | 9.80 g | 9.80 g |
| Cooking salt | 21.00 g | 21.00 g | 21.00 g | 21.00 g |
| Tomato powder | 9.00 g | 9.00 g | 9.00 g | 9.00 g |
| Dry flavor | 2.50 g | 2.50 g | 2.50 g | 2.50 g |
| Silicon dioxide | 0.02 g | 0.02 g | 0.02 g | 0.02 g |
| Vegetable oil | 0.02 g | 0.02 g | 0.02 g | 0.02 g |
| Onion powder | 3.00 g | 3.00 g | 3.00 g | 3.00 g |
| Cream flavor concentrate | 0.03 g | 0.03 g | 0.03 g | 0.03 g |
| Cheese flavor | 0.03 g | 0.03 g | 0.03 g | 0.03 g |
| Tomato flavor conzentrate | 0.04 g | 0.04 g | 0.04 g | 0.04 g |
| Spray-dried composition according to example 1.1 | — | — | 2.80 g | 5.40 g |

6 g of condiment mixture was applied to 94 g of potato chips. With tasting by a panel of trained subjects, the reference preparation A and the sodium glutamate-free preparation D according to the invention were equally rated. As for the preparation C according to the invention, a considerable improvement regarding Umami-taste (and mouthfulness) was likewise observed, compared with the sodium glutamate-reduced reference preparation B.

Example 11

White Sauce

| Ingredient | Reference preparation A | Sodium glutamate-reduced reference preparation B | Sodium glutamate-reduced preparation C according to the invention | Sodium glutamate-free preparation D according to the invention |
|---|---|---|---|---|
| Maltodextrin | 26.28 g | 26.28 g | 26.28 g | 26.28 g |
| Cooking salt | 7.50 g | 7.50 g | 7.50 g | 7.50 g |
| Sodium glutamate | 2.00 g | 0.80 g | 0.80 g | — |
| Vegetable fat | 5.00 g | 5.00 g | 5.00 g | 5.00 g |
| Pepper, white | 0.02 g | 0.02 g | 0.02 g | 0.02 g |
| Onion powder | 1.50 g | 1.50 g | 1.50 g | 1.50 g |
| Pre-pasted corn starch | 30.00 g | 30.00 g | 30.00 g | 30.00 g |
| Fat powder | 27.70 g | 27.70 g | 27.70 g | 27.70 g |
| Spray-dried composition according to example 1.2 | — | — | 2.00 g | 3.60 g |

90 g of sauce mixture was infused with 1000 ml of hot water and strongly stirred using eggbeater. With tasting by a panel of trained subjects, the reference preparation A and the sodium glutamate-free preparation D according to the invention were equally rated. As for the preparation C according to the invention, a considerable improvement regarding Umami-taste (and mouthfulness) was likewise observed, compared with the sodium glutamate-reduced reference preparation B.

Example 12

Brown Sauce

| Ingredient | Reference preparation A | Sodium glutamate-reduced reference preparation B | Sodium glutamate-reduced preparation C according to the invention | Sodium glutamate-free preparation D according to the invention |
|---|---|---|---|---|
| Starch | 40.00 g | 40.00 g | 40.00 g | 40.00 g |
| Maltodextrin | 33.10 g | 33.10 g | 33.10 g | 33.10 g |
| Cooking salt | 6.00 g | 6.00 g | 6.00 g | 6.00 g |
| Sugar coloring (Zuckerkuloer), spray-dried | 5.00 g | 5.00 g | 5.00 g | 5.00 g |
| Yeast extract powder | 3.00 g | 3.00 g | 3.00 g | 3.00 g |
| Sodium glutamate | 2.00 g | 1.30 g | 1.30 g | — |
| Sugar | 0.50 g | 0.50 g | 0.50 g | 0.50 g |
| Fat powder | 5.00 g | 5.00 g | 5.00 g | 5.00 g |
| Tomato powder | 3.00 g | 3.00 g | 3.00 g | 3.00 g |
| Natural vegetable extract | 1.00 g | 1.00 g | 1.00 g | 1.00 g |
| Onion extract | 0.30 g | 0.30 g | 0.30 g | 0.30 g |
| Pepper extract | 0.10 g | 0.10 g | 0.10 g | 0.10 g |
| Dry flavor | 1.00 g | 1.00 g | 1.00 g | 1.00 g |
| Spray-dried composition according to example 1.1 | — | — | 1.40 g | 4.00 g |

90 g of sauce mixture was infused with 1000 ml of hot water and strongly stirred using eggbeater. With tasting by a panel of trained subjects, the reference preparation A and the sodium glutamate-free preparation D according to the invention were equally rated. As for the preparation C according to the invention, a considerable improvement regarding Umami-taste (and mouthfulness) was likewise observed, compared with the sodium glutamate-reduced reference preparation B.

Example 13

Tomato Soup

| Ingredient | Reference preparation A | Sodium glutamate-reduced reference preparation B | Sodium glutamate-reduced preparation C according to the invention | Sodium glutamate-free preparation D according to the invention |
|---|---|---|---|---|
| Water | 50.65 g | 50.65 g | 50.65 g | 50.65 g |
| Vegetable oil | 5.50 g | 5.50 g | 5.50 g | 5.50 g |
| Tomato paste | 24.00 g | 24.00 g | 24.00 g | 24.00 g |
| Cream | 1.05 g | 1.05 g | 1.05 g | 1.05 g |
| Sugar | 2.00 g | 2.00 g | 2.00 g | 2.00 g |
| Cooking salt | 1.70 g | 1.70 g | 1.70 g | 1.70 g |
| Sodium glutamate | 0.40 g | 0.25 g | 0.25 g | — |
| Wheat flour | 5.50 g | 5.50 g | 5.50 g | 5.50 g |
| Starch | 1.20 g | 1.20 g | 1.20 g | 1.20 g |
| cubed tomatoes | 8.00 g | 8.00 g | 8.00 g | 8.00 g |
| Spray-dried composition according to example 1.2 | — | — | 0.40 g | 0.80 g |

The solid ingredients were weighted, mixed and added into water. The vegetable oil was dosed and tomato paste was added. With tasting by a panel of trained subjects, the reference preparation A and the sodium glutamate-free preparation D according to the invention were equally rated. As for the preparation C according to the invention, a considerable improvement regarding Umami-taste (and mouthfulness) was likewise observed, compared with the sodium glutamate-reduced reference preparation B.

Example 14

Application in a Sugar-free Chewing Gum

| part | component | Application in wt.-% |
|---|---|---|
| A | Chewing gum base, Company "Jagum T" | 30.00 |
| B | Sorbitol, pulverized | 39.00 |
|   | Isomalt ® (Palatinit GmbH) | 9.50 |
|   | Xylitol | 2.00 |
|   | Mannite | 3.00 |
|   | Aspartam ® | 0.10 |
|   | Acesulfam ® K | 0.10 |
|   | Emulgum ® (Colloides Naturels, Inc.) | 0.30 |
| C | Sorbitol, 70% | 14.00 |
|   | Glycerin | 1.00 |
| D | Flavoring composition containing 0.1 wt.-% of 2E,4E-decadienoic acid-N-isobutyl amide and 20 wt.-% of cyclopropanecarboxylic acid ((1S,2S,5R)-2-isopropyl-5-methyl-cyclohexyl)-amide (11) | 1 |

Part A to D was mixed and intensively kneaded. The raw mixture can be processed into ready-to-consume chewing gum e.g. in form of thin strip.

Example 15

Application in a Green Tea Drinks

| component | Weight proportion |
|---|---|
| Green tea concentrate | 18.00 |
| 1% solution of a equimolar mixture of formulas (11) and (12) in propylene glycol | 0.40 |
| demineralized water | 81.40 |

The green tea concentrate was mixed with 1 wt-% solution of an equimolar mixture of formula (1) and (2) in propylene glycol. Then this was filled up with demineralized water and again thoroughly stirred. Then the product was filtered, packed in a ready-to consume manner and sterilized at 118° C. The flavor was rated as considerably preferred by a panel of trained subjects, compared with the green tea base which was not flavored.

Example 16

Beef Condiment for Finished-noodle

| component | Weight proportion |
|---|---|
| Beef fat flavor | 5.00 |
| Sugar coloring (Zuckercouleur) | 3.00 |
| Citric acid (anhydrous) | 0.40 |
| Chive (dehydrated) | 2.00 |
| Maltodextrin (ex *Tapoica*) | 10.30 |
| Monosodium glutamate | 15.00 |
| Onion powder | 5.00 |
| Ribotide | 0.80 |
| Sodium chloride | 45.65 |
| Sugar | 2.80 |
| Sweet whey powder | 6.50 |
| Compounds of formula (11) and (12) | 0.05 |

All components were mixed till homogenous mixture was obtained.

Example 17

Finished-noodle with Beef Condiment

| part | component | Weight proportion |
|---|---|---|
| A | Wheat flour | 62.00 |
|   | Potato starch | 10.90 |
| B | Salt | 1.10 |
|   | Guar gum | 0.06 |
|   | Sodium carbonate | 0.07 |
|   | Potasssium carbonate | 0.25 |
|   | $Na_2H_2P_2O_7$ | 0.07 |
|   | Compounds of formula (11) and (12) | 0.05 |
| C | Water | 25.50 |

A suspension of ingredients B in water was added to a mixture of ingredients A and kneaded to a dough. After the dough had been rested for approx. 5 minutes, it was processed into a plate by means of a noodle machine, which was trimmed into common form in the last process step. After 3 minutes of cooking time, the noodle was ready for consumption, and was served with 8 g of beef condiment from application example 12.

Specific Embodiments

A first specific embodiment is directed to use of a compound of Formula (I) or a mixture of compounds of formula (I)

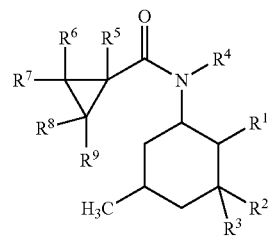

(I)

wherein:
$R^1$, $R^2$, $R^3$ in each case independently of each other represents hydrogen or an alkyl group having 1 to 3 C-atoms, wherein at least one group is not H;
$R^4$ represents hydrogen, an alkyl group having 1 to 6 C-atoms or an alkenyl group having 2 to 6 C-atoms;
$R^5$, $R^6$, $R^7$, $R^8$ in each case independently of each other represents hydrogen or methyl;
$R^9$ represents hydrogen, an alkyl group having 5 to 12 C-atoms or an alkenyl group having 5 to 12 C-atoms;
as a flavoring substance or a mixture of flavoring substances.

Specific embodiment two is directed to a use according to embodiment one, wherein the compound or the compounds of formula (I) is a compound or are compounds selected from the group consisting of:

(1R,3S)-2,2-dimethyl-3-(2-methyl-propenyl)-cyclopropanecarboxylic acid-((1S,2S,5R)-2-isopropyl-5-methyl-cyclohexyl)-amide (1), (1R,3S)-2,2-dimethyl-3-(2-methyl-propenyl)cyclopropanecarboxylic acid-((1R,2R,5S)-2-isopropyl-5-methyl-cyclohexyl)-amide (2), (1S,3R)-2,2-dimethyl-3-(2-methyl-propenyl)-cyclopropanecarboxylic acid-((1S,2S,5R)-2-isopropyl-5-methyl-cyclohexyl)-amide (3), (1S,3R)-2,2-dimethyl-3-(2-methyl-propenyl)cyclopropanecarboxylic acid-((1R,2R,5S)-2-isopropyl-5-methyl-cyclohexyl)-amide (4), (1S,3S)-2,2-dimethyl-3-(2-methyl-propenyl)-cyclopropanecarboxylic acid-((1S,2S,5R)-2-isopropyl-5-methyl-cyclohexyl)-amide (5), (1S,3S)-2,2-dimethyl-3-(2-methyl-propenyl)cyclopropanecarboxylic acid-((1R,2R,5S)-2-isopropyl-5-methyl-cyclohexyl)-amide (6), (1R,3R)-2,2-dimethyl-3-(2-methyl-propenyl)-cyclopropanecarboxylic acid-((1S,2S,5R)-2-isopropyl-5-methyl-cyclohexyl)-amide (7), and (1R,3R)-2,2-dimethyl-3-(2-methyl-propenyl)-cyclopropanecarboxylic acid-((1R,2R,5S)-2-isopropyl-5-methyl-cyclohexyl)amide (8).

Specific embodiment three is directed to the use according to embodiment one, wherein the compound or the compounds of formula (I) is a compound or are compounds of formula (II)

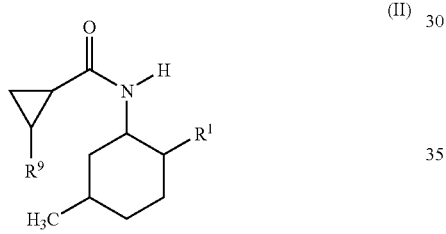

(II)

and wherein:
$R^1$ represents an alkyl group having 1 to 3 C-atoms;
$R^9$ represents hydrogen, an alkyl group having 5 to 12 C-atoms or an alkenyl group having 5 to 12 C-atoms.

Specific embodiment four is directed to use according to embodiment three, wherein the compound or the compounds of formula (II) is a compound or are compounds selected from the group consisting of:
Cyclopropanecarboxylic acid-((1R,2S,5R)-2-isopropyl-5-methyl-cyclohexyl)-amide (9),
Cyclopropanecarboxylic acid-((1S,2R,5S)-2-isopropyl-5-methyl-cyclohexyl)-amide (10),
Cyclopropanecarboxylic acid-((1S,2S,5R)-2-isopropyl-5-methyl-cyclohexyl)-amide (11),
Cyclopropanecarboxylic acid-((1R,2R,5S)-2-isopropyl-5-methyl-cyclohexyl)-amide (12),
Cyclopropanecarboxylic acid-((1R,2R,5R)-2-isopropyl-5-methyl-cyclohexyl)-amide (13),
Cyclopropanecarboxylic acid-((1S,2S,5S)-2-isopropyl-5-methyl-cyclohexyl)-amide (14),
Cyclopropanecarboxylic acid-((1S,2R,5R)-2-isopropyl-5-methyl-cyclohexyl)-amide (15), and
Cyclopropanecarboxylic acid-((1R,2S,5S)-2-isopropyl-5-methyl-cyclohexyl)-amide (16).

Specific embodiment five is directed to use of a compound or a mixture of compounds of formula (I) or (II), as defined in one of the preceding embodiments one to four, for creating, modifying or enhancing an Umami-taste.

Specific embodiment six is directed to a composition, especially a composition suitable for consumption, comprising or consisting of:
 a flavorfully effective amount of one or more compounds of formula (I) or (II) as defined in one of embodiments one to four, and
 one or more ingredients suitable for consumption.

Specific embodiment seven is directed to a composition according to embodiment six, wherein the further ingredients are:
 solid carrier substances or
 solid carrier substances and flavoring components or
 water, an oil phase, one or more W/O emulsifiers, if necessary, one or more anti-oxidants and if necessary, one or more substances for enhancing an antioxidative effect.

Specific embodiment eight is directed to a composition according to embodiment seven, wherein the further ingredients are solid carrier substances, and the weight ratio of total amount of the compounds of formula (I) or (II) as defined in one of embodiments one to four, to the solid carrier substances is in a range from 1:10 to 1:100000, preferably in a range from 1:100 to 1:20000, especially preferably in a range from 1:1000 to 1:5000, based on the dry weight of the composition.

Specific embodiment nine is directed to a composition according to embodiment seven, comprising or consisting of:
 0.01 to 0.1 wt.-% of one or more compounds of formula (I) or (II) as defined in one of claims 1 to 4,
 5 to 30 wt.-% of water,
 50 to 90 wt.-% of an oil phase,
 0.1 to 5 wt.-% of consumable W/O emulsifier and
 if necessary, one or more antioxidants and if necessary, one or more substances for enhancing an antioxidative effect.

Specific embodiment ten is directed to a (i) ready-to-use or ready-to-consume preparation or (ii) semi-finished goods used for nourishment, oral hygiene or enjoyment, comprising
 a flavorfully effective amount of one or more compounds of formula (I) or (II) as defined in one of embodiments one to four, or
 a composition according to one of embodiments six to nine.

Specific embodiment eleven is directed to a ready-to-use or ready-to-consume preparation used for nourishment, oral hygiene or enjoyment according to embodiment ten, comprising 0.01 ppm to 100 ppm, preferably 0.1 ppm to 50 ppm, especially preferably 1 ppm to 30 ppm of one or more compounds of formula (I) or (II) as defined in one of claims 1 to 4, based on the total weight of the ready-to-consume preparation.

Specific embodiment twelve is directed to a composition, preparation or semi-finished goods according to one of embodiment six to eleven, further comprising a substance for masking or reducing an unpleasant taste impression and/or a substance for enhancing the pleasant taste impression of a pleasantly tasting substance.

Specific embodiment thirteen is directed to a method for creating, modifying or enhancing a taste in a (i) ready-to-consume preparation or (ii) semi-finished goods used for nourishment or enjoyment, comprising the following steps:
 mixing a flavorfully effective amount of one or more compounds of formula (I) or (II) as defined in one of embodiments one to four, or a composition according to one of embodiments six to nine or twelve with one or more further ingredients of (i) ready-to-consume preparation or (ii) semi-finished goods
and/or
applying a flavorfully effective amount of one or more compounds of formula (I) or (II) as defined in one of embodiments one to four, or a composition according to one of embodiments six to nine or twelve to one or more further ingredients of (i) ready-to-consume preparation or (ii) semi-finished goods
and/or
embedding a flavorfully effective amount of one or more compounds of formula (I) or (II) as defined in one of embodiments one to four or a composition according to one of embodiments six to nine or twelve in a cladding material or a matrix material.

Specific embodiment fourteen is directed to a method according to embodiment thirteen, for creating, modifying or enhancing an Umami-taste.

Specific embodiment fifteen is directed to a compound of formula (I) or a mixture of compounds of formula (I)

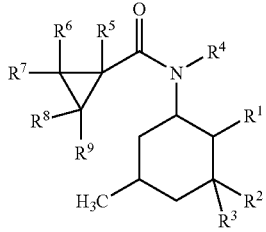

(I)

wherein:
$R^1$, $R^2$, $R^3$ in each case independently of each other represents hydrogen or an alkyl group having 1 to 3 C-atoms, wherein at least one group is not H;
$R^4$ represents hydrogen, an alkyl group having 1 to 6 C-atoms or an alkenyl group having 2 to 6 C-atoms;
$R^5$, $R^6$, $R^7$, $R^8$ in each case independently of each other represents hydrogen or methyl;
$R^9$ represents hydrogen, an alkyl group having 5 to 12 C-atoms or an alkenyl group having 5 to 12 C-atoms;
with the proviso that the compounds of formula (I), which fall within the formula (III), is excluded.

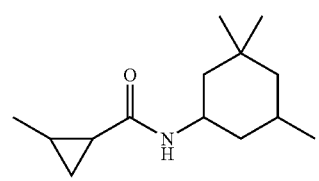

(III)

Specific embodiment sixteen is directed to a compound according to embodiment fifteen or a mixture of the compounds according to embodiment fifteen, wherein the compound or the compounds is a compound or are compounds selected from the group consisting of:
(1R,3S)-2,2-dimethyl-3-(2-methyl-propenyl)-cyclopropanecarboxylic acid-((1S,2S,5R)-2-isopropyl-5-methyl-cyclohexyl)-amide (1), (1R,3S)-2,2-dimethyl-3-(2-methyl-propenyl)cyclopropanecarboxylic acid-((1R,2R,5S)-2-isopropyl-5-methyl-cyclohexyl)-amide (2), (1S,3R)-2,2-dimethyl-3-(2-methyl-propenyl)-cyclopropanecarboxylic acid-((1S,2S,5R)-2-isopropyl-5-methyl-cyclohexyl)-amide (3), (1S,3R)-2,2-dimethyl-3-(2-methyl-propenyl)cyclopropanecarboxylic acid-((1R,2R,5S)-2-isopropyl-5-methyl-cyclohexyl)-amide (4), (1S,3S)-2,2-dimethyl-3-(2-methyl-propenyl)-cyclopropanecarboxylic acid-((1S,2S,5R)-2-isopropyl-5-methyl-cyclohexyl)-amide (5), (1S,3S)-2,2-dimethyl-3-(2-methyl-propenyl)cyclopropanecarboxylic acid-((1R,2R,5S)-2-isopropyl-5-methyl-cyclohexyl)-amide (6), (1R,3R)-2,2-dimethyl-3-(2-methyl-propenyl)-cyclopropanecarboxylic acid-((1S,2S,5R)-2-isopropyl-5-methyl-cyclohexyl)-amide (7), and (1R,3R)-2,2-dimethyl-3-(2-methyl-propenyl)-cyclopropanecarboxylic acid-((1R,2R,5S)-2-isopropyl-5-methyl-cyclohexyl)amide (8).

Specific embodiment seventeen is directed to a compound according to embodiment fifteen or a mixture of the compounds according to embodiment fifteen, wherein the compound or the compounds of formula (I) is a compound or compounds of formula (II)

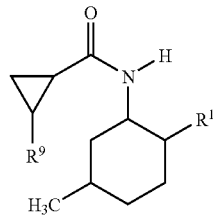

(II)

and wherein:
$R^1$ represents an alkyl group having 1 to 3 C-atoms;
$R^9$ represents hydrogen, an alkyl group having 5 to 12 C-atoms or an alkenyl group having 5 to 12 C-atoms.

Specific embodiment eighteen is directed to a compound according to embodiment seventeen or a mixture of the compounds according to embodiment seventeen, wherein the compound or the compounds of formula (II) is a compound or are compounds selected from the group consisting of:
cyclopropanecarboxylic acid-((1R,2S,5R)-2-isopropyl-5-methyl -cyclohexyl)-amide (9),
cyclopropanecarboxylic acid-((1S,2R,5S)-2-isopropyl-5-methyl -cyclohexyl)-amide (10),
cyclopropanecarboxylic acid-((1S,2S,5R)-2-isopropyl-5-methyl -cyclohexyl)-amide (11),
cyclopropanecarboxylic acid-((1R,2R,5S)-2-isopropyl-5-methyl -cyclohexyl)-amide (12),
cyclopropanecarboxylic acid-((1R,2R,5R)-2-isopropyl-5-methyl -cyclohexyl)-amide (13),
cyclopropanecarboxylic acid-((1S,2S,5S)-2-isopropyl-5-methyl -cyclohexyl)-amide (14),
cyclopropanecarboxylic acid-((1S,2R,5R)-2-isopropyl-5-methyl -cyclohexyl)-amide (15), and
cyclopropanecarboxylic acid-((1R,2S,5S)-2-isopropyl-5-methyl -cyclohexyl)-amide (16).

Specific embodiment nineteen is directed to a method for preparing a compound of formula (11) and/or (12), or a mixture comprising or consisting of the compound of formula (11) and/or (12) as defined in embodiment eighteen, comprising the following steps:
(a) carrying out a Leuckart-Wallach reaction, starting from enantiomerically pure or racemic menthone to a corresponding formamide of formula (III), (III)

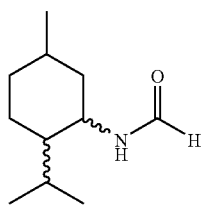

(b) carrying out a fractional crystallization of the neo-menthyl formamides (formula (IV) and/or (V))

(IV)

(V)

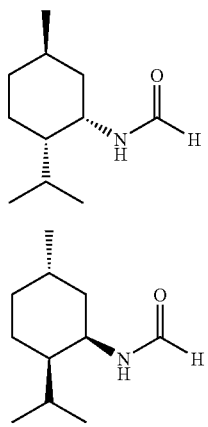

(c) saponifying the neo-menthyl formamides with a strong acid to (VI) and/or (VII), and (VI)

(VII)

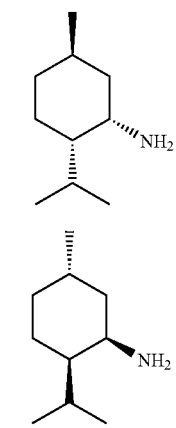

(d) reacting the amine either with (i) cyclopropanecarboxylic acid chloride or with (ii) cyclopropanecarboxylic acid to (11) and/or (12)

(11)

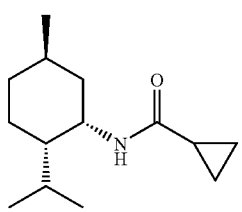

-continued (12)

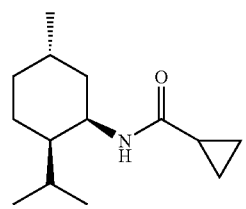

What is claimed is:

1. A compound of formula (I) or a mixture of compounds of formula (I)

(I)

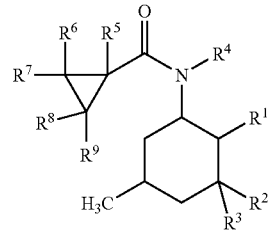

wherein:
$R^1$, $R^2$, and $R^3$ are independently H or an alkyl group having 1 to 3 C-atoms, wherein at least one of $R^1$, $R^2$, and $R^3$ is not H;
$R^4$ is H, an alkyl group having 1 to 6 C-atoms, or an alkenyl group having 2 to 6 C-atoms;
$R^5$, $R^6$, $R^7$, and $R^8$ are independently H or methyl; and
$R^9$ is H, an alkyl group having 5 to 12 C-atoms, or an alkenyl group having 5 to 12 C-atoms;
with the proviso that compounds of formula (III), (III)

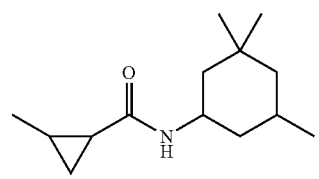

are excluded.

2. A compound according to claim 1 or a mixture of the compounds according to claim 1, wherein the compound or the compounds are selected from the group consisting of:
(1R,3S)-2,2-dimethyl-3-(2-methyl-propenyl)-cyclopropanecarboxylic acid-((1S,2S,5R)-2-isopropyl-5-methyl-cyclohexyl)-amide (1), (1R,3S)-2,2-dimethyl-3-(2-methyl-propenyl)-cyclopropanecarboxylic acid-((1R,2R,5S)-2-isopropyl-5-methyl-cyclohexyl)-amide (2), (1S,3R)-2,2-dimethyl-3-(2-methyl-propenyl)-cyclopropanecarboxylic acid-((1S,2S,5R)-2-isopropyl-5-methyl-cyclohexyl)-amide (3), (1S,3R)-2,2-dimethyl-3-(2-methyl-propenyl)-cyclopropanecarboxylic acid-((1R,2R,5S)-2-isopropyl-5-methyl-cyclohexyl)-amide (4), (1S,3S)-2,2-dimethyl-3-(2-methyl-propenyl)-cyclopropanecarboxylic acid-((1S,2S,5R)-2-isopropyl-5-methyl-cyclohexyl)-amide (5), (1S,3S)-2,2-dimethyl-3-(2-methyl-propenyl)cyclopropanecarboxylic acid-((1R,2R,5S)-2-isopropyl-5-methyl-cyclohexyl)-amide (6), (1R,3R)-2,2-dimethyl-3-(2-methyl-propenyl)-cyclopropanecarboxylic acid-((1S,2S,5R)-2-isopropyl-5-methyl-cyclohexyl)-amide (7), and (1R,3R)-2,2-dimethyl-3-(2-methylpropenyl)-cyclopropanecarboxylic acid-((1R,2R,5S)-2-isopropyl-5-methyl-cyclohexyl)amide (8).

3. A compound according to claim 1 or a mixture of the compounds according to claim 1, wherein the compound or the compounds of formula (I) is a compound or compounds of formula (II)

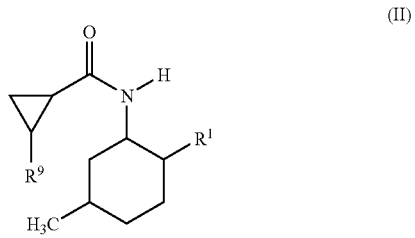

(II)

and wherein:
$R^1$ is alkyl group having 1 to 3 C-atoms; and
$R^9$ is H, an alkyl group having 5 to 12 C-atoms, or an alkenyl group having 5 to 12 C-atoms.

4. A compound according to claim 3 or a mixture of the compounds according to claim 3, wherein the compound or the compounds of formula (II) is a compound or are compounds selected from the group consisting of:
cyclopropanecarboxylic acid((1R,2S,5R)-2-isopropyl-5-methyl-cyclohexyl)-amide (9),
cyclopropanecarboxylic acid((1S,2R,5S)-2-isopropyl-5-methyl-cyclohexyl)-amide (10),
cyclopropanecarboxylic acid((1S,2S,5R)-2-isopropyl-5-methyl-cyclohexyl)-amide (11),
cyclopropanecarboxylic acid((1R,2R,5S)-2-isopropyl-5-methyl-cyclohexyl)-amide (12),
cyclopropanecarboxylic acid((1R,2R,5R)-2-isopropyl-5-methyl-cyclohexyl)-amide (13),
cyclopropanecarboxylic acid((1S,2S,5S)-2-isopropyl-5-methyl-cyclohexyl)-amide (14),
cyclopropanecarboxylic acid((1S,2R,5R)-2-isopropyl-5-methyl-cyclohexyl)-amide (15), and
cyclopropanecarboxylic acid((1R,2S,5S)-2-isopropyl-5-methyl-cyclohexyl)-amide (16).

5. A composition suitable for consumption, comprising:
a flavorfully effective amount of one or more compounds of formula (I) according to claim 1, and
one or more ingredients suitable for consumption.

6. A composition according to claim 5, wherein the further ingredients are:
solid carrier substances or
solid carrier substances and flavoring components or
water, an oil phase, optionally one or more W/O emulsifiers, one or more antioxidants and optionally, one or more substances for enhancing an antioxidative effect.

7. A composition according to claim 6, wherein the further ingredients are solid carrier substances, and the weight ratio of total amount of the compounds of formula (I) according to claim 1, to the solid carrier substances is in a range from 1:10 to 1:100000 based on the dry weight of the composition.

8. A composition according to claim 7, comprising:
0.01 to 0.1 wt % of one or more compounds of formula (I),
5 to 30 wt % of water,
50 to 90 wt % of an oil phase,
0.1 to 5 wt % of consumable W/O emulsifier and optionally, one or more antioxidants and, optionally, one or more substances for enhancing an antioxidative effect.

9. The composition according to claim 5, further comprising a substance for masking or reducing an unpleasant taste impression and/or a substance for enhancing the pleasant taste impression of a pleasantly tasting substance.

10. A (i) ready-to-use or ready-to-consume preparation or (ii) semi-finished goods used for nourishment, oral hygiene or enjoyment, comprising
a flavorfully effective amount of one or more compounds of formula (I)

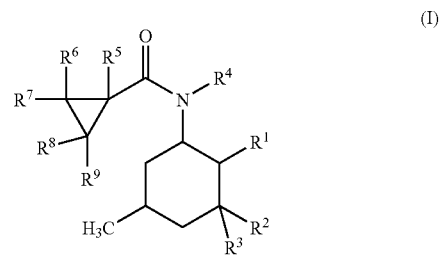

(I)

wherein:
$R^1$, $R^2$, and $R^3$ are independently H or an alkyl group having 1 to 3 C-atoms, wherein at least one of $R^1$, $R^2$, and $R^3$ is not H;
$R^4$ is H, an alkyl group having 1 to 6 C-atoms, or an alkenyl group having 2 to 6 C-atoms;
$R^5$, $R^6$, $R^7$, and $R^8$ are independently H or methyl; and
$R^9$ is H, an alkyl group having 5 to 12 C-atoms, or an alkenyl group having 5 to 12 C-atoms;
wherein the compound or mixture of compounds is a flavoring substance or a mixture of flavoring substances.

11. A ready-to-use or ready-to-consume preparation used for nourishment, oral hygiene or enjoyment according to claim 10, comprising 0.01 ppm to 100 ppm of one or more compounds of formula (I), based on the total weight of the ready-to-consume preparation.

12. A composition, preparation or semi-finished goods according to claim 10, further comprising a substance for masking or reducing an unpleasant taste impression and/or a substance for enhancing the pleasant taste impression of a pleasantly tasting substance.

13. A method for creating, modifying or enhancing a taste in a (i) ready-to-consume preparation or (ii) semi-finished goods used for nourishment or enjoyment, comprising the following steps:
mixing a flavorfully effective amount of one or more compounds of formula (I) according to claim 1 with one or more further ingredients of (i) a ready-to-consume preparation or (ii) semi-finished goods
and/or
applying a flavorfully effective amount of one or more compounds of formula (I) according to claim 1 to one or more further ingredients of (i) ready-to-consume preparation or (ii) semi-finished goods
and/or
embedding a flavorfully effective amount of one or more compounds of formula (I) according to claim 1 in a cladding material or a matrix material.

14. The method according to claim 13, further comprising creating, modifying or enhancing an Umami-taste.

15. A method for preparing a compound of formula (11) and/or (12), or a mixture comprising the compound of formula (11) and/or (12), comprising the following steps:

(a) carrying out a Leuckart-Wallach reaction, starting from enantiomerically pure or racemic menthone to produce a corresponding formamide of formula (III),

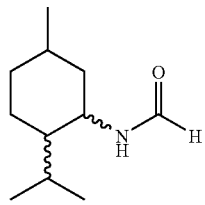

(III)

(b) carrying out a fractional crystallization of the neo-menthyl formamides (formula (IV) and/or (V))

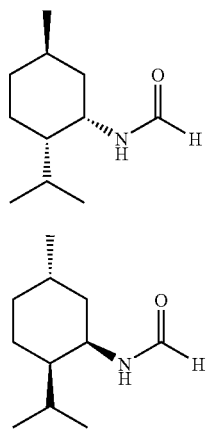

(IV)

(V)

(c) saponifying the neo-menthyl formamides with a strong acid to produce amine (VI) and/or (VII), and

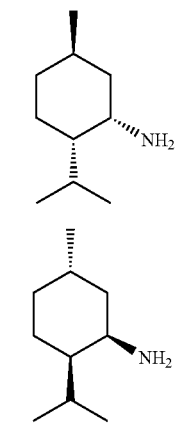

(VI)

(VII)

(d) reacting the amine VI and/or VII either with (i) cyclopropanecarboxylic acid chloride or with (ii) cyclopropanecarboxylic acid to produce (11) and/or (12)

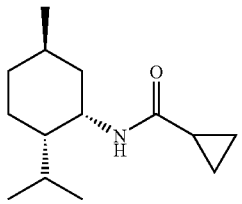

(11)

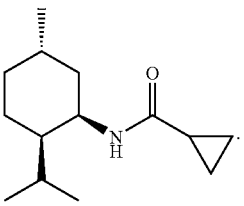

(12)

16. A method for flavoring a material comprising adding to the material a compound of Formula (I) or a mixture of compounds of formula (I)

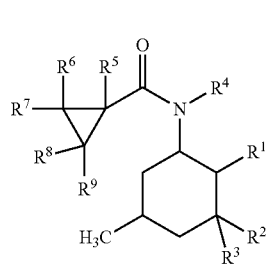

(I)

wherein:
$R^1$, $R^2$, and $R^3$ are independently H or an alkyl group having 1 to 3 C-atoms, wherein at least one of $R^1$, $R^2$, and $R^3$ is not H;
$R^4$ is H, an alkyl group having 1 to 6 C-atoms, or an alkenyl group having 2 to 6 C-atoms;
$R^5$, $R^6$, $R^7$, and $R^8$ are independently H or methyl; and
$R^9$ is H, an alkyl group having 5 to 12 C-atoms, or an alkenyl group having 5 to 12 C-atoms;
wherein the compound or mixture of compounds is a flavoring substance or a mixture of flavoring substances.

17. The method according to claim 16, wherein the compound or the compounds of formula (I) is a compound or are compounds selected from the group consisting of:
(1R,3S)-2,2-dimethyl-3-(2-methyl-propenyl)-cyclopropanecarboxylic acid-((1S,2S,5R)-2-isopropyl-5-methyl-cyclohexyl)-amide (1), (1R,3S)-2,2-dimethyl-3-(2-methyl-propenyl)-cyclopropanecarboxylic acid-((1R,2R,5S)-2-isopropyl-5-methyl-cyclohexyl)-amide (2), (1S,3R)-2,2-dimethyl-3-(2-methyl-propenyl)-cyclopropanecarboxylic acid-((1S,2S,5R)-2-isopropyl-5-methyl-cyclohexyl)-amide (3), (1S,3R)-2,2-dimethyl-3-(2-methyl-propenyl)-cyclopropanecarboxylic acid-((1R,2R,5S)-2-isopropyl-5-methyl-cyclohexyl)-amide (4), (1S,3S)-2,2-dimethyl-3-(2-methyl-propenyl)-cyclopropanecarboxylic acid-((1S,2S,5R)-2-isopropyl-5-methyl-cyclohexyl)-amide (5), (1S,3S)-2,2-dimethyl-3-(2-methyl-propenyl)-cyclopropanecarboxylic acid-((1R,2R,5S)-2-isopropyl-5-methyl-cyclohexyl)-amide (6), (1R,3R)-2,2-dimethyl-3-(2-methyl-propenyl)-cyclopropanecarboxylic acid-((1S,2S,5R)-2-isopropyl-5-methyl-cyclohexyl)-amide (7), and (1R,3R)-2,2-dimethyl-3-(2-methylpropenyl)-cyclopropanecarboxylic acid-((1R,2R,5S)-2-isopropyl-5-methyl-cyclohexyl)-amide (8).

18. The method according to claim 16, wherein the compound or the compounds of formula (I) is a compound or are compounds of formula (II)

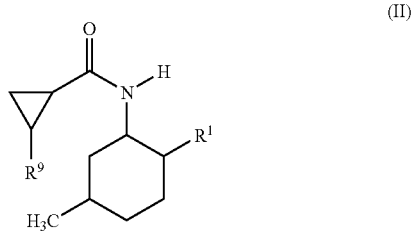

and wherein:
$R^1$ is an alkyl group having 1 to 3 C-atoms; and
$R^9$ is H, an alkyl group having 5 to 12 C-atoms, or an alkenyl group having 5 to 12 C-atoms.

19. The method according to claim 18, wherein the compound or the compounds of formula (II) is a compound or are compounds selected from the group consisting of:
Cyclopropanecarboxylic acid ((1R,2S,5R)-2-isopropyl-5-methyl-cyclohexyl)-amide (9),
Cyclopropanecarboxylic acid ((1S,2R,5S)-2-isopropyl-5-methyl-cyclohexyl)-amide (10),
Cyclopropanecarboxylic acid ((1S,2S,5R)-2-isopropyl-5-methyl-cyclohexyl)-amide (11),
Cyclopropanecarboxylic acid ((1R,2R,5S)-2-isopropyl-5-methyl-cyclohexyl)-amide (12),
Cyclopropanecarboxylic acid ((1R,2R,5R)-2-isopropyl-5-methyl-cyclohexyl)-amide (13),
Cyclopropanecarboxylic acid ((1S,2S,5S)-2-isopropyl-5-methyl-cyclohexyl)-amide (14),
Cyclopropanecarboxylic acid ((1S,2R,5R)-2-isopropyl-5-methyl-cyclohexyl)-amide (15), and
Cyclopropanecarboxylic acid ((1R,2S,5S)-2-isopropyl-5-methyl-cyclohexyl)-amide (16).

* * * * *

UNITED STATES PATENT AND TRADEMARK OFFICE
CERTIFICATE OF CORRECTION

PATENT NO. : 7,919,133 B2  
APPLICATION NO. : 12/117438  
DATED : April 5, 2011  
INVENTOR(S) : Jan Looft et al.

It is certified that error appears in the above-identified patent and that said Letters Patent is hereby corrected as shown below:

In the Claims:

At column 45, claim number 2, line numbers 3-4, should be corrected to read:

ethyl-3-(2-methyl-propenyl)-cyclopropanecarboxylic acid-((1R,2R,5S)-2-isopropyl-5-methyl-cyclohexyl)-

Signed and Sealed this
Thirty-first Day of May, 2011

David J. Kappos
*Director of the United States Patent and Trademark Office*